(12) United States Patent
Okamoto et al.

(10) Patent No.: US 10,876,993 B2
(45) Date of Patent: Dec. 29, 2020

(54) AMMONIA GAS SENSOR AND METHOD FOR MEASURING CONCENTRATION OF AMMONIA GAS

(71) Applicant: NGK INSULATORS, LTD., Nagoya (JP)

(72) Inventors: Taku Okamoto, Nagoya (JP); Takayuki Sakurai, Kakamigahara (JP); Noriko Hirata, Nagoya (JP); Yuki Nakayama, Nagoya (JP)

(73) Assignee: NGK INSULATORS, LTD., Nagoya (JP)

( * ) Notice: Subject to any disclaimer, the term of this patent is extended or adjusted under 35 U.S.C. 154(b) by 528 days.

(21) Appl. No.: 15/370,069

(22) Filed: Dec. 6, 2016

(65) Prior Publication Data
US 2017/0184538 A1 Jun. 29, 2017

(30) Foreign Application Priority Data

Dec. 24, 2015 (JP) ................. 2015-251134
Apr. 15, 2016 (JP) ................. 2016-082117
May 23, 2016 (JP) ................. 2016-102130

(51) Int. Cl.
*G01N 27/407* (2006.01)
*G01N 27/30* (2006.01)
(Continued)

(52) U.S. Cl.
CPC ....... *G01N 27/4074* (2013.01); *G01N 27/301* (2013.01); *G01N 27/4067* (2013.01);
(Continued)

(58) Field of Classification Search
CPC ....... G01N 27/404–407; G01N 27/409; G01N 27/419; G01N 27/41; G01N 27/4045;
(Continued)

(56) References Cited

U.S. PATENT DOCUMENTS 8,133,370 B2    3/2012 Roessler et al.
2003/0205078 A1† 11/2003 Hasei
(Continued)

FOREIGN PATENT DOCUMENTS

DE    10 2016 222 432 A1    5/2017
EP       2 372 358 B1       2/2015
(Continued)

OTHER PUBLICATIONS

English machine translation of JP2003-035693 (Year: 2003).*
(Continued)

*Primary Examiner* — Gurpreet Kaur
(74) *Attorney, Agent, or Firm* — Global IP Counselors, LLP

(57) ABSTRACT

Provided is a gas sensor which is capable of preferably sensing an ammonia gas, and has excellent durability. A mixed-potential gas sensor includes a sensor element composed of an oxygen-ion conductive solid electrolyte, and a heater provided inside the element. The sensor element includes on a surface thereof a sensing electrode formed of a cermet including Pt, Au and an oxygen-ion conductive solid electrolyte, and also includes a reference electrode formed of a cermet of Pt and an oxygen-ion conductive solid electrolyte, and a porous electrode protective layer whose porosity is 5 to 40% covering at least the sensing electrode. The Au abundance ratio in a surface of noble metal particles forming the sensing electrode is 0.4 or more. The concentration of an ammonia gas is determined on the basis of a potential difference occurring between the sensing electrode and the reference electrode when the sensor element is disposed in a measurement gas and heated to 400° C. to 800° C.

27 Claims, 14 Drawing Sheets

(51) Int. Cl.
*G01N 27/406* (2006.01)
*G01N 33/00* (2006.01)
(52) U.S. Cl.
CPC ..... *G01N 27/4075* (2013.01); *G01N 27/4076* (2013.01); *G01N 27/4077* (2013.01); *G01N 33/0054* (2013.01); *Y02A 50/20* (2018.01)
(58) Field of Classification Search
CPC .......................... G01N 27/4074; G01M 15/10; G01M 15/102; G01M 15/104; F01N 2560/00–20
See application file for complete search history.

(56) References Cited

U.S. PATENT DOCUMENTS

| | | |
|---|---|---|
| 2007/0080074 A1 | 4/2007 | Wang et al. |
| 2007/0215469 A1 | 9/2007 | Imamura |
| 2009/0114539 A1 | 5/2009 | Ziegler et al. |
| 2009/0301876 A1* | 12/2009 | Wagner ................. G01N 27/30 204/415 |
| 2010/0243447 A1 | 9/2010 | Fujisaki et al. |
| 2015/0013431 A1 | 1/2015 | Kakimoto et al. |
| 2017/0138891 A1 | 5/2017 | Hirata et al. |

FOREIGN PATENT DOCUMENTS

| | | | |
|---|---|---|---|
| EP | 2 980 574 A1 | | 2/2016 |
| JP | 2003-35693 A | | 2/2003 |
| JP | 2003-035693 A | † | 2/2003 |
| JP | 2003-185625 A | | 7/2003 |
| JP | 2005-83817 A | | 3/2005 |
| JP | 2007-248351 A | | 9/2007 |
| JP | 2009-511859 A | | 3/2009 |
| JP | 4293579 B2 | | 7/2009 |
| JP | 2010-256344 A | | 11/2010 |
| JP | 2011-47756 A | | 3/2011 |
| JP | 491447 B2 | | 1/2012 |
| JP | 4914447 B2 | | 1/2012 |
| JP | 2012-211928 A | | 11/2012 |
| JP | 5097239 B2 | | 12/2012 |
| JP | 2015-034814 A | † | 2/2015 |
| JP | 2015-34814 A | | 2/2015 |
| WO | 2007/044302 A2 | | 4/2007 |

OTHER PUBLICATIONS

The Official Communication of the Third Party Observations for the corresponding German patent Application No. 102016225567.3, dated Mar. 27, 2018.

A Written Opposition to the Grant of Patent submitted for the corresponding Japanese Patent No. 5965564, dated Feb. 10, 2017.

\* cited by examiner
† cited by third party

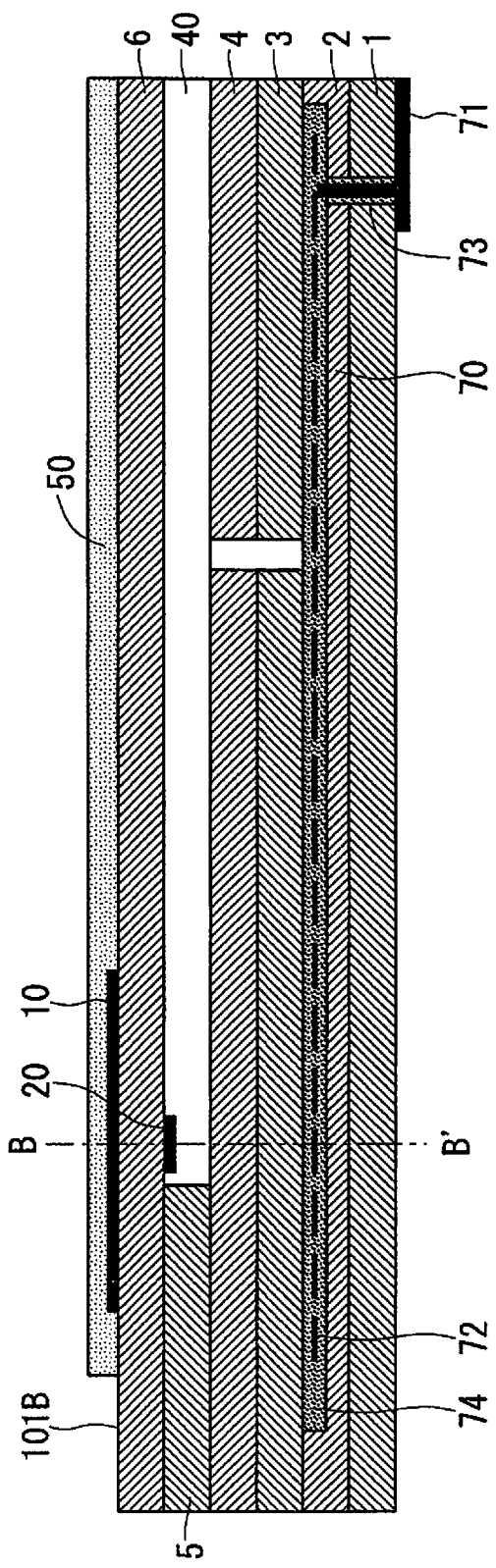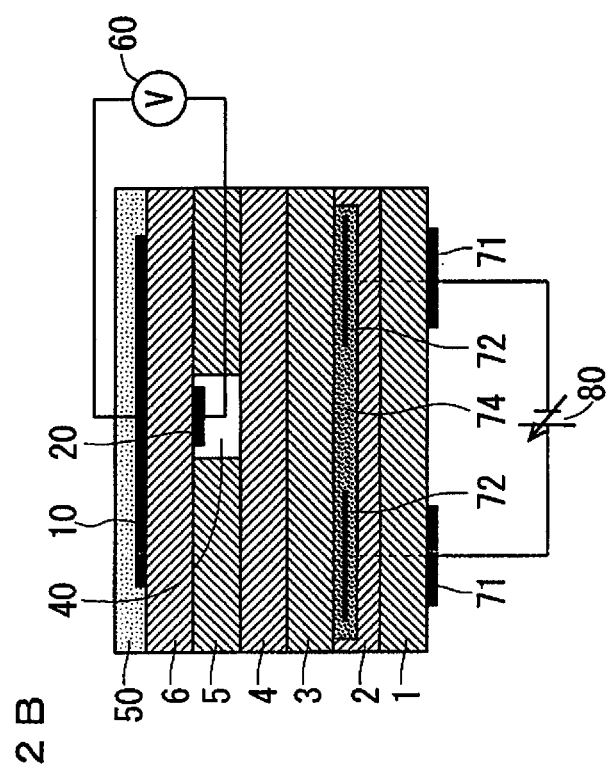

F I G . 6
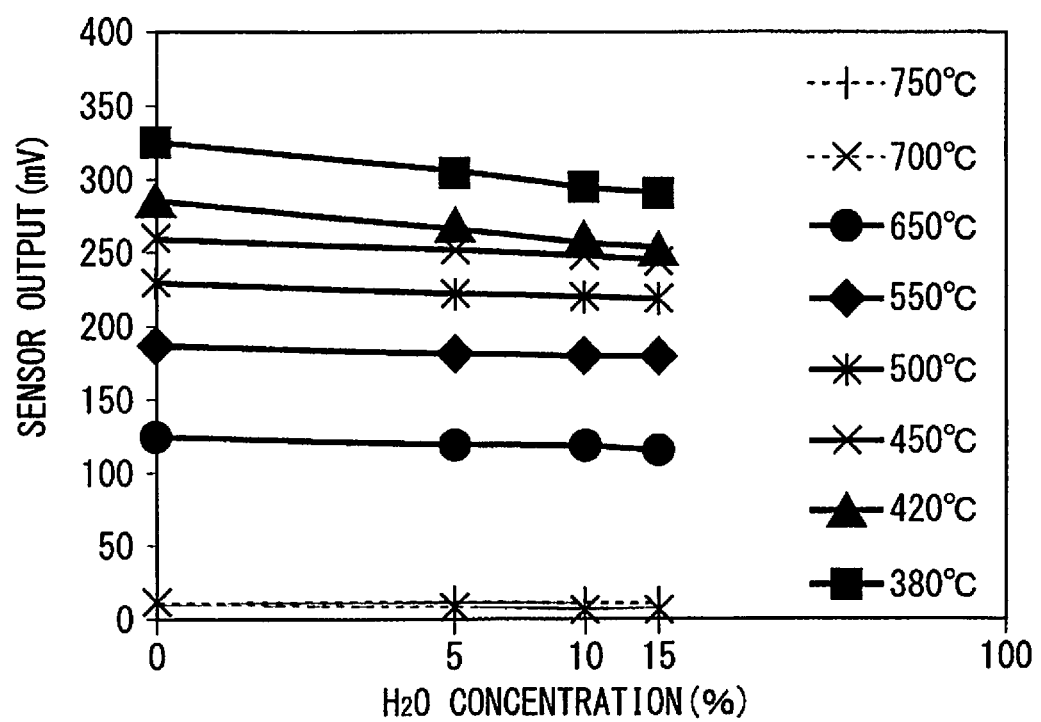

AMMONIA GAS SENSOR AND METHOD FOR MEASURING CONCENTRATION OF AMMONIA GAS

BACKGROUND OF THE INVENTION

Field of the Invention

The present invention relates to a gas sensor for sensing an ammonia gas.

Description of the Background Art

Gas sensors that sense a predetermined gas component of a measurement gas to determine its concentration come in various types such as semiconductor gas sensor, catalytic combustion gas sensor, oxygen-concentration difference sensing gas sensor, limiting current gas sensor, and mixed-potential gas sensor. Some of these gas sensors include a sensor element mainly composed of ceramic being a solid electrolyte such as zirconia.

Among the above-mentioned gas sensors, mixed-potential gas sensors that target an ammonia gas as a component to be sensed are classified broadly into gas sensors in which a metal oxide is used as a material of a sensing electrode (for example, see Japanese Unexamined Patent Application Publication (Translation of PCT Application) No. 2009-511859); gas sensors in which a composite oxide including gold and a metal oxide is used as a material of a sensing electrode (for example, see Japanese Patent Application Laid-Open No. 2011-47756); and gas sensors in which a noble metal is used as a material of a sensing electrode (for example, see Japanese Patent No. 4914447 and Japanese Patent Application Laid-Open No. 2012-211928).

As ammonia gas sensors that do not use a mixed potential, those that sense an ammonia gas by measuring an impedance of a sensible portion have been known (for example, see Japanese Patent Application Laid-Open No. 2005-83817).

There is a need for reliably sensing a very small amount (e.g. 100 ppm or less) of an ammonia gas contained in an exhaust gas from an internal combustion engine such as an automobile engine. However, while sensor elements of gas sensors for meeting such a need are always exposed to a high-temperature exhaust gas atmosphere, they are not necessarily disposed in an easily replaceable manner, and they are therefore desired to have durability (long-term reliability).

Numerous studies have been conducted on ammonia gas sensors with a sensing electrode formed of a metal oxide like the ammonia gas sensor disclosed in Japanese Unexamined Patent Application Publication (Translation of PCT Application) No. 2009-511859, but all of these ammonia gas sensors have the problem that they cannot endure an automobile exhaust environment in view of durability (adhesion and stability) of electrodes.

For the ammonia gas sensor disclosed in Japanese Patent Application Laid-Open No. 2011-47756, sensitivity variation caused by $H_2O$ in a detection gas is recognized to be small, but there is a problem in durability because a composite oxide is used in a sensing electrode. Further, there is the problem that the ammonia gas sensor is not suitable for automobile exhaust gas applications in which a high-temperature gas is an object to be measured because the melting points of Au (gold) and $BiVO_4$ used as main constituent materials of the composite oxide are 1064° C. and 947° C., respectively.

The gas sensor disclosed in Japanese Patent No. 4914447 is a mixed-potential gas sensor which has a sensing electrode formed of a noble metal and is capable of measuring an ammonia gas with high sensitivity, where a gas component concentration is determined on the premise that both of a first electrode and a second electrode have catalytic activation, which is different in degree between the first electrode and the second electrode, though.

Specifically, the first electrode is formed by applying a Pt—Au paste to a sensor element, and then integrally firing (co-firing) the paste with a solid electrolyte that forms the sensor element, and the second electrode has a two-layer structure formed by applying a Pt paste to a sensor element and co-firing the paste with a solid electrolyte, followed by performing Au-plating. The first electrode exhibits a "remarkable catalytic action," whereas the second electrode exhibits a "slight catalytic action." Since it is thought to be an Au-plated portion that actually contributes to an electrochemical reaction in the second electrode, it can be said that the second electrode is not an alloy electrode, but an electrode with an Au composition ratio of substantially 100%, namely an Au electrode, as regards at least the portion that contributes to the electrochemical reaction.

The gas sensor disclosed in Japanese Patent Application Laid-Open No. 2012-211928 employs Au as a noble metal component of a sensing electrode, and the sensing electrode is formed by so called secondary firing in which firing is performed after a paste is applied to a fired solid electrolyte body. A selective reaction layer formed of a metal oxide is provided on a sensing electrode for securing ammonia gas selectivity.

Au has a low melting point, and hence a high vapor pressure, and cannot be singly co-fired with a solid electrolyte body. Accordingly, an Au electrode is formed by plating or secondary firing in the techniques disclosed in Japanese Patent No. 4914447 and Japanese Patent Application Laid-Open No. 2012-211928, but these aspects have a problem in long-term reliability because Au may be desorbed from a sensor element in a high temperature state at the time of using a gas sensor.

For stably using an Au electrode, it is effective that Au is alloyed with Pt to elevate the melting point, and the alloy is co-fired with a solid electrolyte body, but there is the problem that ammonia is burned due to catalytic activation of Pt if the amount of Pt in the electrode is excessively large.

The inventors of the present invention have made intensive studies to find out that when a Pt—Au alloy having an increased Au abundance ratio on a surface is used as a metal component of a sensing electrode of a gas sensor, catalytic activation against an ammonia gas is disabled while the sensing electrode can be co-fired with a solid electrolyte body, so that a mixed potential having correlation with the concentration of an ammonia gas can be induced. Such finding has led the inventors to a mixed-potential gas sensor which is capable of sensing an ammonia gas with high sensitivity, and has durability.

For securing detection sensitivity to an ammonia gas, it is important to reduce interference from other gases, particularly influences of hydrocarbons, and $H_2O$ that is considered as a problem also in Japanese Patent Application Laid-Open No. 2011-47756.

SUMMARY OF THE INVENTION

The present invention relates to a gas sensor for sensing an ammonia gas, and is directed particularly to suppression of interference from other gases.

According to the present invention, a mixed-potential gas sensor for sensing an ammonia gas in a measurement gas includes a sensor element composed of an oxygen-ion conductive solid electrolyte, the sensor element including: a sensing electrode formed of a cermet of a noble metal and an oxygen-ion conductive solid electrolyte, the sensing electrode being provided on a surface of the sensor element; a reference electrode formed of a cermet of Pt and an oxygen-ion conductive solid electrolyte; and an electrode protective layer being a porous layer that covers at least the sensing electrode. The noble metal includes Pt and Au. The Au abundance ratio is 0.4 or more, the Au abundance ratio being an area ratio of a portion covered with the Au to a portion at which the Pt is exposed in a surface of noble metal particles forming the sensing electrode. The porosity of the electrode protective layer is 5% or more and 40% or less. The gas sensor determines the concentration of the ammonia gas on the basis of a potential difference between the sensing electrode and the reference electrode.

According to the present invention, there is provided an ammonia gas sensor which is capable of preferably sensing an ammonia gas, and has excellent durability, with reduced influences of interference from other gas components including at least hydrocarbon gases.

Preferably, the ammonia gas sensor further includes: a heater which is provided inside the sensor element, and heats the sensor element. The ammonia gas sensor has the sensor element which is disposed in the measurement gas and heated to an element control temperature of 400° C. or higher and 800° C. or lower by the heater, and determines the concentration of the ammonia gas on the basis of a potential difference occurring between the sensing electrode and the reference electrode.

According to the present invention, there is provided an ammonia gas sensor with reduced influences of interference from water vapor in addition to hydrocarbon gases.

According to another aspect of the present invention, a mixed-potential gas sensor for sensing an ammonia gas in a measurement gas includes: a sensor element composed of an oxygen-ion conductive solid electrolyte; and a heater which is provided inside the sensor element, and heats the sensor element. The sensor element includes: a sensing electrode formed of a cermet of a noble metal and an oxygen-ion conductive solid electrolyte, the sensing electrode being provided on a surface of the sensor element; and a reference electrode formed of a cermet of Pt and an oxygen-ion conductive solid electrolyte. The noble metal includes Pt and Au. The Au abundance ratio is 0.4 or more, the Au abundance ratio being an area ratio of a portion covered with the Au to a portion at which the Pt is exposed in a surface of noble metal particles forming the sensing electrode. The sensor element is disposed in the measurement gas and heated to an element control temperature of 450° C. or higher and lower than 700° C. by the heater. The ammonia gas sensor determines the concentration of the ammonia gas on the basis of a potential difference occurring between the sensing electrode and the reference electrode.

According to the present invention, there is provided an ammonia gas sensor which is capable of preferably sensing an ammonia gas, and has excellent durability, with reduced influences of interference from other gas components including water vapor.

An object of the present invention is to provide a gas sensor which is capable of preferably sensing an ammonia gas, and has excellent durability.

These and other objects, features, aspects and advantages of the present invention will become more apparent from the following detailed description of the present invention when taken in conjunction with the accompanying drawings.

BRIEF DESCRIPTION OF THE DRAWINGS

FIGS. 2A and 2B are schematic cross-sectional views schematically showing an example configuration of a gas sensor 100B being a modification of the gas sensor 100A;

FIG. 6 shows a change of the sensor output with respect to the concentration of water vapor at each element control temperature, which is plotted, where the gas sensor 100A is driven at different element control temperatures under a plurality of gas atmospheres having the same concentration of an ammonia gas and different concentrations of water vapor;

DESCRIPTION OF THE PREFERRED EMBODIMENTS

<First Configuration>

Figure 1A:
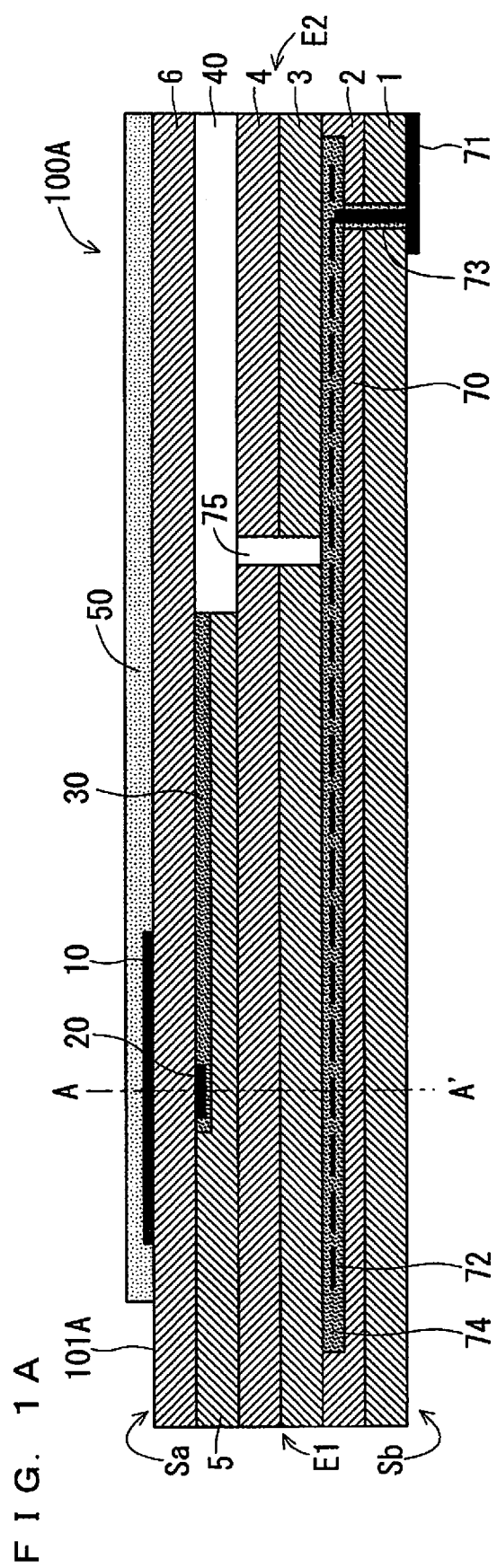
FIGS. 1A and 1B are schematic cross-sectional views schematically showing an example configuration of a gas sensor 100A according to a first configuration.
Figure 1B:
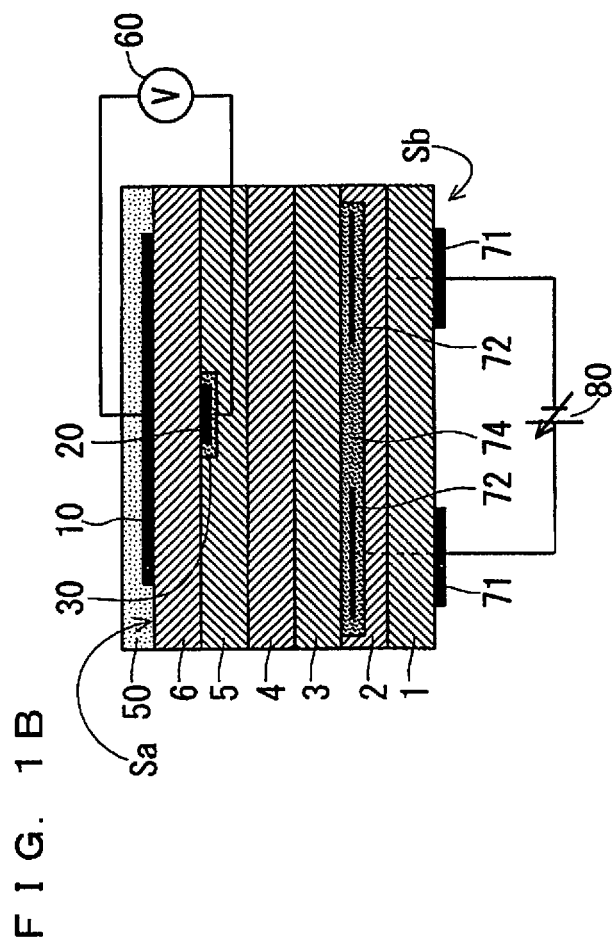

FIGS. 1A and 1B are schematic sectional views schematically illustrating an example configuration of a gas sensor 100A according to a first configuration of the present invention. FIG. 1A is a vertical sectional view of a sensor element 101A, which is a main component of the gas sensor 100A, taken along the longitudinal direction of the sensor element 101A. FIG. 1B is a view including a cross-section of the sensor element 101A perpendicular to the longitudinal direction of the sensor element 101A at a position A-A' of FIG. 1A.

The gas sensor 100A according to the first configuration of the present invention is a so-called mixed-potential gas sensor. Generally speaking, the gas sensor 100A determines the concentration of a gas component, which is a measurement target, in a measurement gas using a potential difference that occurs between a sensing electrode 10, which is provided on the surface of the sensor element 101A mainly made of ceramic that is an oxygen-ion conductive solid electrolyte such as zirconia ($ZrO_2$), and a reference electrode 20, which is provided inside the sensor element 101A, due to a difference in the concentration of the gas component between the portions near the electrodes based on the principle of mixed potential.

More specifically, the gas sensor 100A preferably determines the concentration of an ammonia ($NH_3$) gas in a measurement gas, where the measurement gas is an exhaust gas present in an exhaust pipe of an internal combustion engine such as a diesel engine or a gasoline engine.

The sensor element 101A mainly includes a reference gas introduction layer 30, a reference gas introduction space 40, and a surface protective layer 50 in addition to the sensing electrode 10 and the reference electrode 20 described above.

In the first configuration of the present invention, the sensor element 101A has the structure in which six layers, namely, a first solid electrolyte layer 1, a second solid electrolyte layer 2, a third solid electrolyte layer 3, a fourth solid electrolyte layer 4, a fifth solid electrolyte layer 5, and a sixth solid electrolyte layer 6, each formed of an oxygen-ion conductive solid electrolyte, are laminated in the stated order from the bottom side of FIGS. 1A and 1B. The sensor element 101A additionally includes other components mainly between these layers or on an outer peripheral surface of the element. The solid electrolytes constituting these six layers are fully airtight. Such a sensor element 101A is manufactured by, for example, laminating ceramic green sheets corresponding to the individual layers, which have been subjected to a predetermined process and printing of a circuit pattern, and further, by integrating the laminated layers through firing.

The gas sensor 100A does not necessarily need to include the sensor element 101A formed of such a laminated body including the six layers. The sensor element 101A may be formed as a laminated body having more or fewer layers or may not have a laminated structure.

In the following description, for convenience' sake, the surface located as the upper surface of the sixth solid electrolyte layer 6 in FIGS. 1A and 1B is referred to as a front surface Sa of the sensor element 101A, and the surface located as the lower surface of the first solid electrolyte layer 1 in FIGS. 1A and 1B is referred to as a rear surface Sb of the sensor element 101A. In the determination of the concentration of the ammonia gas in a measurement gas with the gas sensor 100A, a predetermined range starting from a distal end E1 being one end of the sensor element 101A, which includes at least the sensing electrode 10, is disposed in a measurement gas atmosphere; the other portion including a base end E2 opposite to the distal end E1 is disposed so as not to be in contact with the measurement gas atmosphere.

The sensing electrode 10 is an electrode for sensing a measurement gas. The sensing electrode 10 is formed as a porous cermet electrode made of Pt containing a predetermined ratio of Au, namely, Pt—Au alloy and zirconia. The sensing electrode 10 is provided in a substantially rectangular shape in plan view at a position closer to the distal end E1 that is one end in the longitudinal direction of the sensor element 101A on the front surface Sa of the sensor element 101A. The gas sensor 100A is placed such that, in its use, the sensor element 101A corresponding to at least the portion in which the sensing electrode 10 is provided is exposed to a measurement gas.

The catalytic activity of the sensing electrode 10 against an ammonia gas is disabled over a predetermined concentration range by preferably determining the composition of the Pt—Au alloy being its constituent material. That is, the decomposition reaction of an ammonia gas is prevented or reduced in the sensing electrode 10. In the gas sensor 100A, accordingly, the potential of the sensing electrode 10 selectively varies with respect to (has correlation with) the ammonia gas in the predetermined concentration range, in accordance with its concentration. In other words, the sensing electrode 10 is provided so as to have high dependence of potential on concentration for an ammonia gas in the predetermined concentration range while having low dependence of potential on concentration for other components of the measurement gas.

More specifically, in the sensor element 101A of the gas sensor 100A according to the first configuration of the present invention, the sensing electrode 10 is provided so as to have a preferably determined Au abundance ratio in the surface of the Pt—Au alloy particles included in the sensing electrode 10, thereby exhibiting a strong dependence of potential on concentration of an ammonia gas in at least the concentration range of 0 ppm to 100 ppm. This means that the sensing electrode 10 is provided to preferably sense an ammonia gas in a concentration range of 0 ppm to 100 ppm.

In this specification, the Au abundance ratio means an area ratio of the portion covered with Au to a portion at which Pt is exposed in the surface of noble metal particles included in the sensing electrode 10. In this specification, the Au abundance ratio is calculated from an expression below $$\text{Au abundance ratio} = \text{Au detection value}/\text{Pt detection value} \quad (1)$$

where Au and Pt detection values are values in an Auger spectrum obtained by performing a measurement on the surface of the noble metal particles by Auger electron spectroscopy (AES).

The Au abundance ratio can also be calculated using a relative sensitivity coefficient method from a peak intensity of a peak detected for Au and Pt, which is obtained by subjecting the surface of noble metal particles to X-ray photoelectron spectroscopy (XPS) analysis. The value of the Au abundance ratio obtained by this method can be considered to be substantially the same as the value of the Au abundance ratio calculated on the basis of AES analysis.

The sensing electrode 10 will be described below in detail.

The reference electrode 20 is an electrode having a substantially rectangular shape in plan view, which is provided inside the sensor element 101A and serves as a reference in the determination of the concentration of the measurement gas. The reference electrode 20 is provided as a porous cermet electrode of Pt and zirconia.

It suffices that the reference electrode 20 has a porosity of 10% or more and 30% or less and a thickness of 5 μm or more and 15 μm or less. The plane size of the reference electrode 20 may be smaller than that of the sensing electrode 10 as illustrated in FIGS. 1A and 1B, or may be equal to that of the sensing electrode 10 as in a second configuration, which will be described below (see FIGS. 3A and 3B).

The reference gas introduction layer 30 is a layer made of porous alumina, which is provided inside the sensor element 101A to cover the reference electrode 20. The reference gas introduction space 40 is an internal space provided near the base end E2 of the sensor element 101A. Air (oxygen), serving as a reference gas in the determination of the concentration of an ammonia gas, is externally introduced into the reference gas introduction space 40.

The reference gas introduction space 40 and the reference gas introduction layer 30 are in communication with each other, and accordingly, in the use of the gas sensor 100A, the surrounding of the reference electrode 20 is always filled with air (oxygen) through the reference gas introduction space 40 and the reference gas introduction layer 30. During the use of the gas sensor 100A, thus, the reference electrode 20 always has a constant potential.

The reference gas introduction space 40 and the reference gas introduction layer 30 are provided so as not to come into contact with a measurement gas owing to their surrounding solid electrolytes. This prevents the reference electrode 20 from coming into contact with the measurement gas even when the sensing electrode 10 is exposed to the measurement gas.

In the case illustrated in FIG. 1A, the reference gas introduction space 40 is provided in such a manner that part of the fifth solid electrolyte layer 5 is in communication with the exterior on the base end E2 of the sensor element 101A. The reference gas introduction layer 30 is provided so as to extend in the longitudinal direction of the sensor element 101A between the fifth solid electrolyte layer 5 and the sixth solid electrolyte layer 6. The reference electrode 20 is provided under the center of gravity of the sensing electrode 10 with reference to FIGS. 1A and 1B.

The surface protective layer 50 is a porous layer made of alumina, which is provided so as to cover at least the sensing electrode 10 on the front surface Sa of the sensor element 101A. The surface protective layer 50 is provided as an electrode protective layer that prevents or reduces the degradation of the sensing electrode 10 due to continuous exposure to a measurement gas during the use of the gas sensor 100A. In the case illustrated in FIGS. 1A and 1B, the surface protective layer 50 is provided so as to cover not only the sensing electrode 10 but also substantially the entire front surface Sa of the sensor element 101A except for a predetermined range starting from the distal end E1.

The surface protective layer 50 may be provided so as to have a thickness of 10 μm to 50 μm, and may have a pore size of 1 μm or less, and the porosity of the surface protective layer 50 is preferably 5% or more and 40% or less. It is not preferable that the porosity is less than 5% because the measurement gas does not preferably arrive at the sensing electrode 10, and thus the responsiveness of the gas sensor 100A deteriorates. It is not preferable that the porosity is more than 40% because a poisoning substance easily sticks to the sensing electrode 10, and thus a function of protecting the sensing electrode 10 cannot be sufficiently performed.

When the porosity of the surface protective layer 50 is 40% or less, the surface protective layer 50 also exhibits such an effect that influences of interference from other gas components can be suppressed, as described later.

In this preferred embodiment, the porosity is evaluated by analyzing an enlarged cross-sectional SEM image (secondary electron image) (by referencing descriptions in Nobuyasu Mizutani et. al, "Ceramic Processing" (GIHODO SHUPPAN Co., Ltd.)).

As illustrated in FIG. 1B, the gas sensor 100A is equipped with a potentiometer 60 capable of measuring a potential difference between the sensing electrode 10 and the reference electrode 20. Although FIG. 1B schematically illustrates wiring of the sensing electrode 10, the reference electrode 20, and the potentiometer 60, in an actual sensor element 101A, connection terminals (not shown) are provided correspondingly to the respective electrodes on the front surface Sa or the rear surface Sb on the base end E2 side, and wiring patterns (not shown), which connect the respective electrodes and their corresponding connection terminals, are formed on the front surface Sa and inside the element. The sensing electrode 10 and the reference electrode 20 are electrically connected with the potentiometer 60 through the wiring patterns and the connection terminals. Hereinbelow, a potential difference between the sensing electrode 10 and the reference electrode 20, which is measured by the potentiometer 60, is also referred to as a sensor output.

The sensor element 101A further includes a heater part 70, which performs temperature control of heating the sensor element 101A and maintaining the temperature of the sensor element 101A, to enhance the oxygen ion conductivity of the solid electrolyte. The heater part 70 includes a heater electrode 71, a heater 72, a through hole 73, a heater insulating layer 74, and a pressure diffusion hole 75.

The heater electrode 71 is an electrode formed while being in contact with the rear surface Sb of the sensor element 101A (in FIGS. 1A and 1B, the lower surface of the first solid electrolyte layer 1). The heater part 70 is electrically connected with an external power supply 80, so that it can be powered from the external power supply 80 through the heater electrode 71.

The heater 72 is an electric resistor provided inside the sensor element 101A. The heater 72 is connected with the heater electrode 71 through the through hole 73 and generates heat by being powered externally via the heater electrode 71 to heat the solid electrolytes forming the sensor element 101A and maintain their temperatures.

In the case illustrated in FIGS. 1A and 1B, the heater 72 is buried while being vertically sandwiched between the second solid electrolyte layer 2 and the third solid electrolyte layer 3 so as to extend from the base end E2 to the position below the sensing electrode 10 near the distal end E1. The value of a voltage applied to the heater 72 by the external power source 80 is appropriately controlled by control means (not shown) to flow a heater current according to a desired temperature, thereby enabling the adjustment of the entire sensor element 101A to the temperature at which the solid electrolytes are activated.

The heater insulating layer 74 is an insulating layer formed of an insulator such as alumina on the upper and lower surfaces of the heater 72. The heater insulating layer 74 is formed for electrical insulation between the second solid electrolyte layer 2 and the heater 72 and for electrical insulation between the third solid electrolyte layer 3 and the heater 72.

The pressure diffusion hole 75 is a part provided to penetrate the third solid electrolyte layer 3 and the fourth solid electrolyte layer 4 and to be in communication with the reference gas introduction space 40, and is formed to mitigate an internal pressure rise associated with a temperature rise in the heater insulating layer 74.

In the determination of the concentration of an ammonia gas in a measurement gas using the gas sensor 100A having such a configuration, as described above, air (oxygen) is supplied to the reference gas introduction space 40, with the sensor element 101A in only a predetermined range, which starts from the distal end E1 and includes at least the sensing electrode 10, being disposed in a space containing a measurement gas, and with the sensor element 101A on the base end E2 being apart from the space. The heater 72 heats the sensor element 101A to a predetermined temperature of 400° C. or higher and 800° C. or lower, preferably 450° C. or higher and lower than 750° C., more preferably 450° C. or higher and 650° C. or lower. The temperature of the sensor element 101A being heated by the heater 72 is also referred to as an element control temperature. In this preferred embodiment, the element control temperature is evaluated from the surface temperature of the sensing electrode 10. The surface temperature of the sensing electrode 10 can be evaluated by infrared thermography.

In a state described above, a potential difference occurs between the sensing electrode 10 exposed to the measurement gas and the reference electrode 20 exposed to the air. As described above, however, the potential of the reference electrode 20 disposed in the air (having a constant oxygen concentration) atmosphere is maintained at a constant potential, whereas the potential of the sensing electrode 10 selectively has a dependence on concentration for the ammonia gas in the measurement gas. The potential difference (sensor output) is thus substantially a value according to the composition of the measurement gas present around the sensing electrode 10. Therefore, a certain functional relationship (referred to as sensitivity characteristics) holds between the concentration of the ammonia gas and the sensor output. In the description below, such sensitivity characteristics may also be referred to as, for example, sensitivity characteristics for the sensing electrode 10.

In the actual determination of the concentration of an ammonia gas, in advance, a plurality of different mixed gases, each of which has a known concentration of an ammonia gas, are used as the measurement gas, and the sensitivity characteristics are experimentally identified by performing a measurement on the sensor output for each measurement gas. In the actual use of the gas sensor 100A, accordingly, an operation processor (not shown) converts the sensor output, which varies from moment to moment in accordance with the concentration of an ammonia gas in a measurement gas, into the concentration of the ammonia gas based on the sensitivity characteristics. The concentration of the unburned hydrocarbon gas in the measurement gas can thus be determined almost in real time.

Modification of First Configuration

FIGS. 2A and 2B are schematic sectional views schematically illustrating an example configuration of a gas sensor 100B, which is a modification of the gas sensor 100A. FIG. 2A is a vertical sectional view of a sensor element 101B, which is a main component of the sensor element 101B, taken along the longitudinal direction of the gas sensor 100B. FIG. 2B is a view including a cross-section of the sensor element 101B perpendicular to the longitudinal direction of the sensor element 101B at a position B-B' of FIG. 2A.

The gas sensor 100B is provided in such a manner that the reference gas introduction space 40 of the sensor element 101A of the gas sensor 100A is extended to below the sensing electrode 10, whereas the reference gas introduction layer 30 is omitted and the reference electrode 20 is exposed to the reference gas introduction space 40. The other configurational elements are similar to those of the gas sensor 100A. Thus, the way how a sensor output occurs is the same as in the case of the gas sensor 100A. In other words, similarly to the gas sensor 100A, the gas sensor 100B is a so-called mixed-potential gas sensor.

The gas sensor 100B having the configuration as described above, which includes the sensor element 101B and has sensitivity characteristics determined in advance similarly to the gas sensor 100A, can determine the concentration of an ammonia gas in a measurement gas.

Second Configuration

Figure 3A:
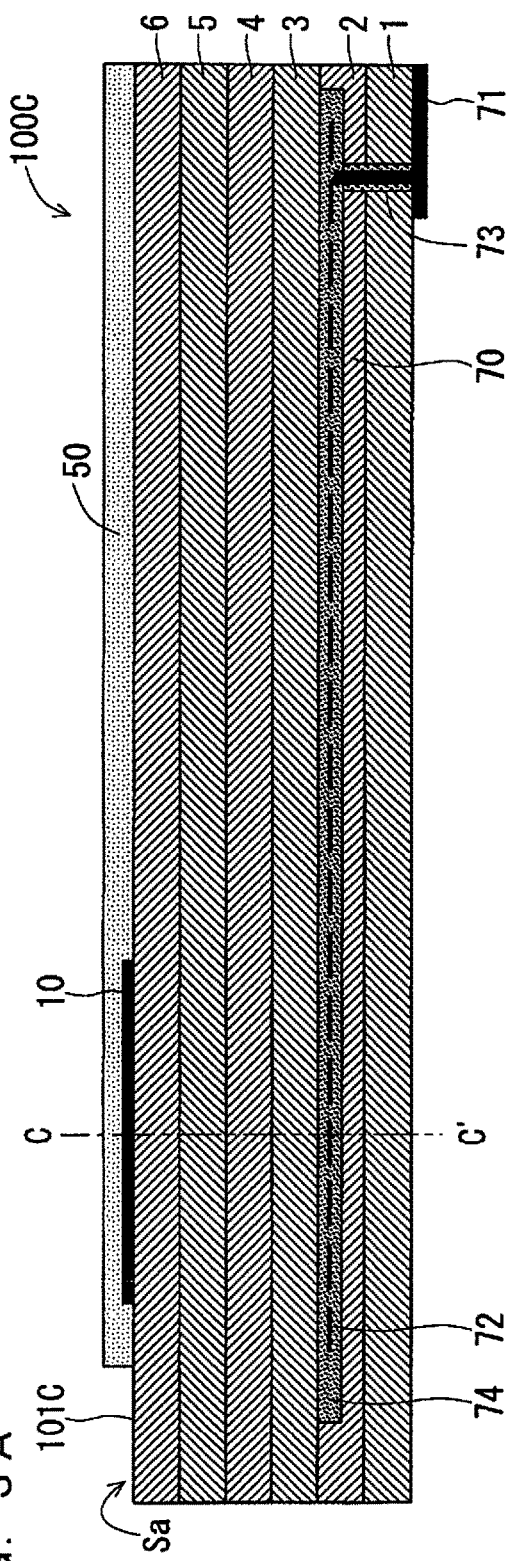
FIGS. 3A and 3B are schematic cross-sectional views schematically showing an example configuration of a gas sensor 100C according to a second configuration.
Figure 3B:
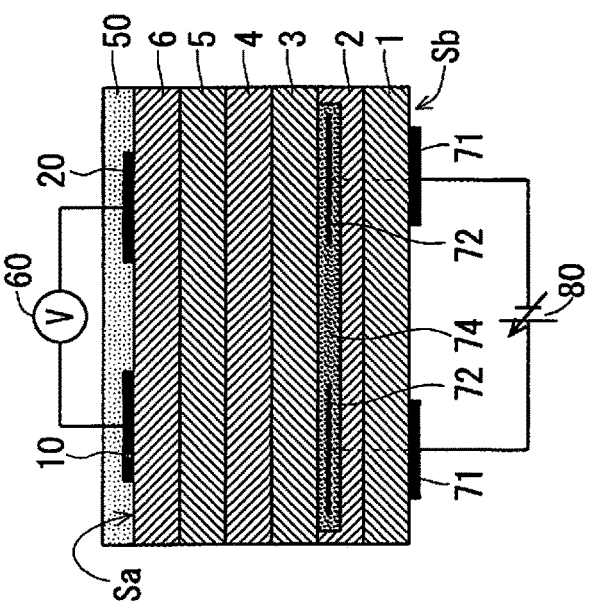

FIGS. 3A and 3B are schematic sectional views schematically illustrating a configuration example of a gas sensor 100C according to a second configuration of the present invention. FIG. 3A is a vertical sectional view of a sensor element 101C, which is a main component of the gas sensor 100C, taken along the longitudinal direction of the sensor element 101C. FIG. 3B is a view including a cross-section of the sensor element 101C perpendicular to the longitudinal direction of the sensor element 101C at a position C-C' of FIG. 3A.

The gas sensor 100C is also a so-called mixed-potential gas sensor similarly to the gas sensors 100A and 100B. In the sensor element 101C of the gas sensor 100C, however, not only the sensing electrode 10 but also the reference electrode 20 is disposed on the front surface Sa of the sensor element 101C and is covered with the surface protective layer 50, differently from the sensor element 101A and the sensor element 101B. The constituent materials for the respective electrodes of the gas sensor 100C are the same as those of the gas sensors 100A and 100B.

The gas sensor 100C includes no reference gas introduction space 40 (further, no reference gas introduction layer 30) and no pressure diffusion hole 75. The other components of the gas sensor 100C are similar to those of the gas sensors 100A and 100B. Although the sensing electrode 10 and the reference electrode 20 are provided at the same position in the longitudinal direction of the gas sensor 100C (see FIG. 3B) in the case illustrated in FIGS. 3A and 3B, these electrodes may be disposed at different positions, for example, may be disposed in the longitudinal direction of the sensor element 101C.

In the determination of the concentration of an ammonia gas in a measurement gas using the gas sensor 100C having such a configuration, the sensor element 101C is disposed in such a manner that the reference electrode 20 as well as the sensing electrode 10 is exposed to the measurement gas, unlike the gas sensors 100A and 100B. Although the sensing electrode 10 and the reference electrode 20 are accordingly exposed to the same atmosphere, the constituent materials for the respective electrodes are the same as those for the gas sensors 100A and 100B. In the gas sensor 100C, thus, the potential of the sensing electrode 10 varies selectively with respect to the concentration of an ammonia gas as in the gas sensors 100A and 100B. Unlike the sensing electrode 10, the catalytic activity of the reference electrode 20, which is formed as a porous cermet electrode of Pt and zirconia, is not prevented or reduced against a specific gas component. As a result, the sensing electrode 10 and the reference electrode 20 are identical in behavior toward gas components other than the ammonia gas. Thus, the sensor output of the gas sensor 100C substantially varies in accordance with an unburned hydrocarbon gas present in a measurement gas.

Similarly to the gas sensors 100A and 100B, thus, the gas sensor 100C whose sensitivity characteristics have been identified in advance can determine the concentration of an ammonia gas in a measurement gas.

<Details of Sensing Electrode>

As described above, in the gas sensors 100A to 100C, the sensing electrode 10 is formed such that its catalytic activation against an ammonia gas is disabled over a predetermined concentration range. This is implemented by including gold (Au) in the sensing electrode 10 as a conductive component (a noble metal component), in addition to platinum (Pt) being a main constituent.

As the Au abundance ratio increases, Au tends to be concentrated on the surface of noble metal particles forming the sensing electrode 10. More specifically, an Au-riched Pt—Au alloy tends to be formed near the surface of Pt-riched Pt—Au alloy particles. An increase in this tendency leads to an increase in tendency of disabling catalytic activation in the sensing electrode 10.

Figure 4:
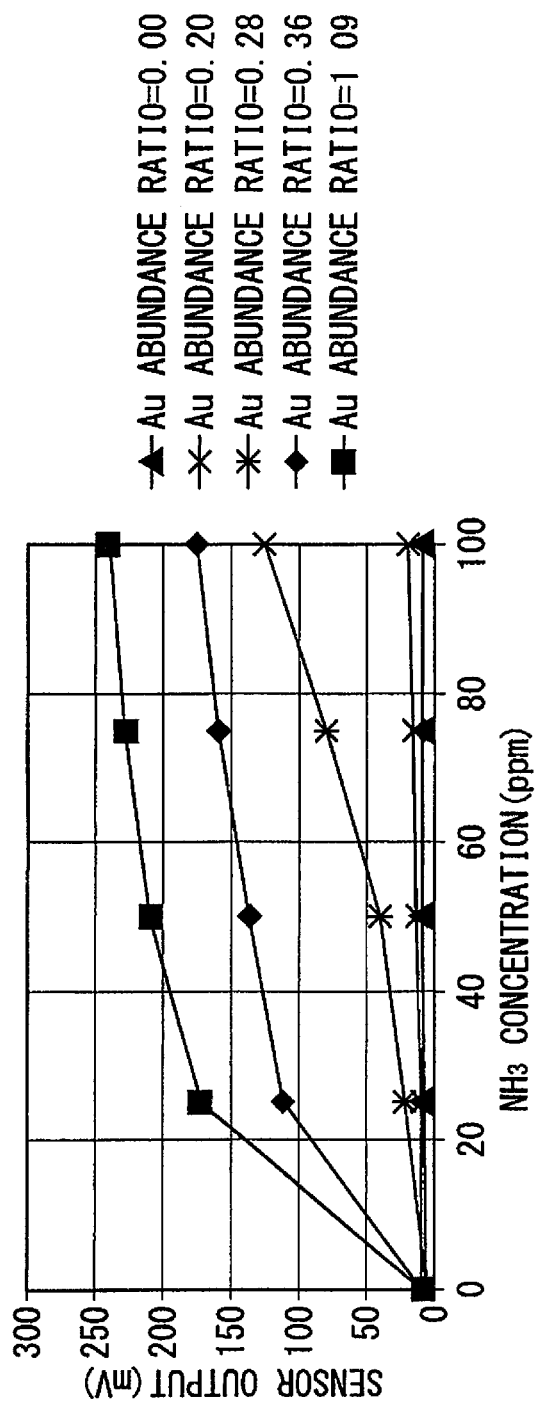
FIG. 4 illustrates sensitivity characteristics in five sensor elements 101A having mutually different Au abundance ratios in a sensing electrode 10.

FIG. 4 illustrates sensitivity characteristics (change of the sensor output with respect to the concentration of an ammonia gas) in five sensor elements 101A having mutually different Au abundance ratios in the sensing electrode 10. Conditions for measurement of the sensor output when such sensitivity characteristics are obtained, and conditions for analysis of the Au abundance ratio are as follows. The Au abundance ratio shown in FIG. 4 is an average of values calculated in accordance with the equation (1) from the results of AES analysis at mutually different three points of a noble metal portion existing on a rupture surface of the sensing electrode 10.

(Conditions for Measurement of Sensor Output)
Element control temperature: 500° C.;
Gas atmosphere: $O_2$=10%, $H_2O$=5%, $NH_3$=0-100 ppm (25 ppm step), balance: $N_2$;
Gas flow rate: 0.5 L/min;
Pressure: 1 atm;
Surface protective layer: porosity: 12%, thickness: 10 μm.
(Conditions for Analysis of Au Abundance Ratio)
Apparatus: field emission Auger electron spectrometer (SAM 680 manufactured by Physical Electronics, Inc. in U.S.)
Measurement Condition: accelerating voltage: 20 keV;
Analysis region: about 50 nm φ (spot analysis of noble metal particles exposed to surface of sensing electrode 10).

FIG. 4 shows that when the Au abundance ratio in the sensing electrode 10 is 0 (i.e. the metal component in the sensing electrode includes only Pt) or 0.20, the graph is flat, i.e. a sensor output cannot be obtained at all even at a high ammonia gas concentration.

However, when the Au abundance ratio is 0.28, the graph is sloped on the high concentration side, and when the Au abundance ratio is 0.36 or 1.09, the output is noticeably changed on the low concentration side, and the value of the sensor output becomes higher as the ammonia gas concentration increases also on the high concentration side.

By setting the Au abundance ratio in the sensing electrode 10 to 0.4 or more in light of the above-mentioned relationship between the Au abundance ratio in the sensing electrode 10 and the sensitivity characteristics of the gas sensor, the above-described gas sensors 100A to 100C make it possible to measure the ammonia gas concentration in a low concentration range of 0 ppm to 100 ppm.

When the Au abundance ratio is excessively increased, it becomes difficult to form the sensing electrode 10, and also the melting point of the sensing electrode 10 as a whole decreases. Therefore, the Au abundance ratio may be at most 2.4 for ensuring that the sensing electrode 10 preferably functions.

The reason why as shown in FIG. 4, dependence of the sensor output on concentration is noticeable on the high concentration side when the Au abundance ratio is low, and dependence of the sensor output on concentration is noticeable on the low concentration side when the Au abundance ratio is high may be that in the former case, the sensing electrode 10 includes a large amount of Pt, and therefore ammonia in an exhaust gas is burned due to catalytic activation of Pt before the ammonia arrives at a three-phase interface and causes an electrochemical reaction, whereas in the latter case, a part of ammonia in an exhaust gas is not burned and arrives at a three-phase interface in an unburned state, and therefore an electrochemical reaction occurs, leading to induction of a potential.

The volume ratio between noble metal components and zirconia in the sensing electrode 10 may be about from 4:6 to 8:2.

For allowing the gas sensors 100A to 100C to preferably exhibit their functions, the porosity of the sensing electrode 10 is preferably 10% or more and 30% or less, and the thickness of the sensing electrode 10 is preferably 5 μm or more.

The plane size of the sensing electrode 10 may be appropriately set, and it suffices that, for example, the length in the longitudinal direction of the sensor element is about 2 mm to 10 mm and the length in the perpendicular direction to the longitudinal direction is about 1 mm to 5 mm.

<Suppression of Interference from Other Gas Components>

Since the gas sensors 100A to 100C target an ammonia gas as an object to be sensed, ideally the sensor output thereof is desired to reflect only the concentration of an ammonia gas. This means, in other words, that it is desirable that the sensing electrode 10 is provided so as to have high dependence of the potential on concentration for an ammonia gas while having no dependence of the potential on concentration for other components of a measurement gas.

However, in the gas sensors 100A to 100C, the principle of a mixed potential is employed, and therefore when the measurement gas includes not only an ammonia gas but also other gas components which induce a mixed potential comparable to that of the ammonia gas, an output value (a potential difference between the sensing electrode 10 and the reference electrode 20) derived from such other gas components may be superimposed on the obtained sensor output in principle. That is, interference from other gas components may occur in the sensor output. When such interference occurs, the calculated value of the concentration of an ammonia gas is larger than an actual value. Thus, for securing measurement accuracy, influences of other gas components are desired to be suppressed as much as possible even if the concentration of such other gas components is reflected in the sensor output. In practice, interference from a hydrocarbon gas and water vapor ($H_2O$ gas) is apt to cause a problem.

(Interference from Hydrocarbon Gas)

Figure 5A:
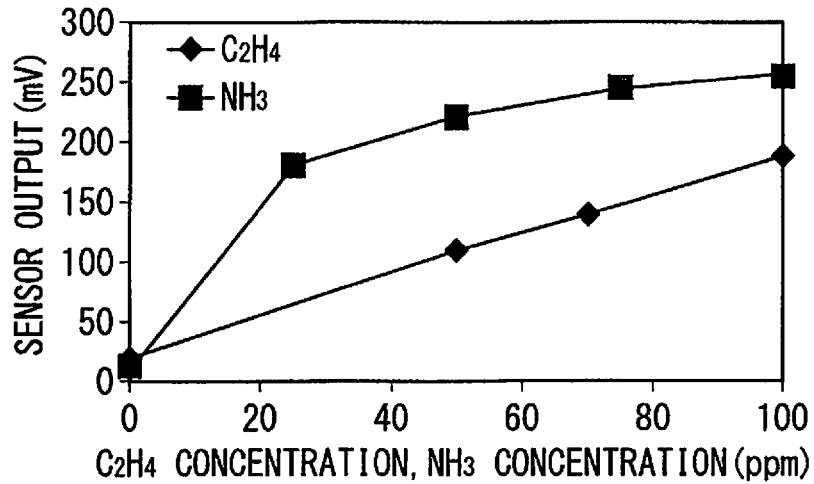
FIGS. 5A, 5B and 5C show sensitivity characteristics to an ammonia gas and sensitivity characteristics to an ethylene gas for three gas sensors 100A having different porosities of a surface protective layer 50.
Figure 5B:
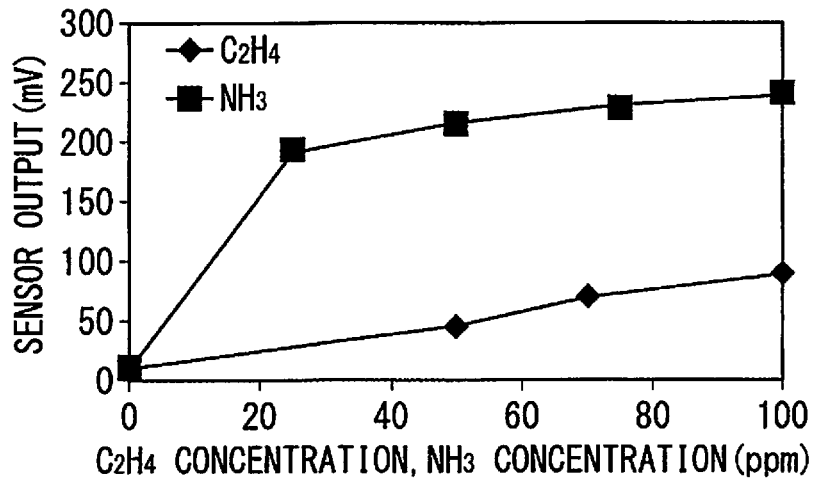
Figure 5C:
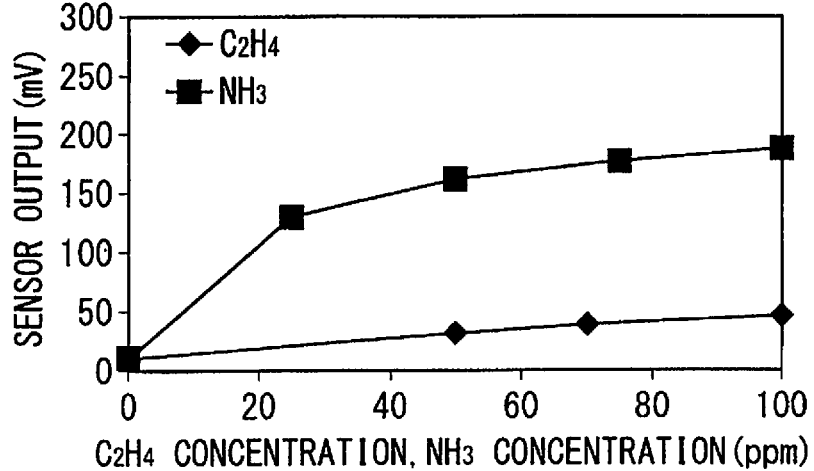
Figure 7A:
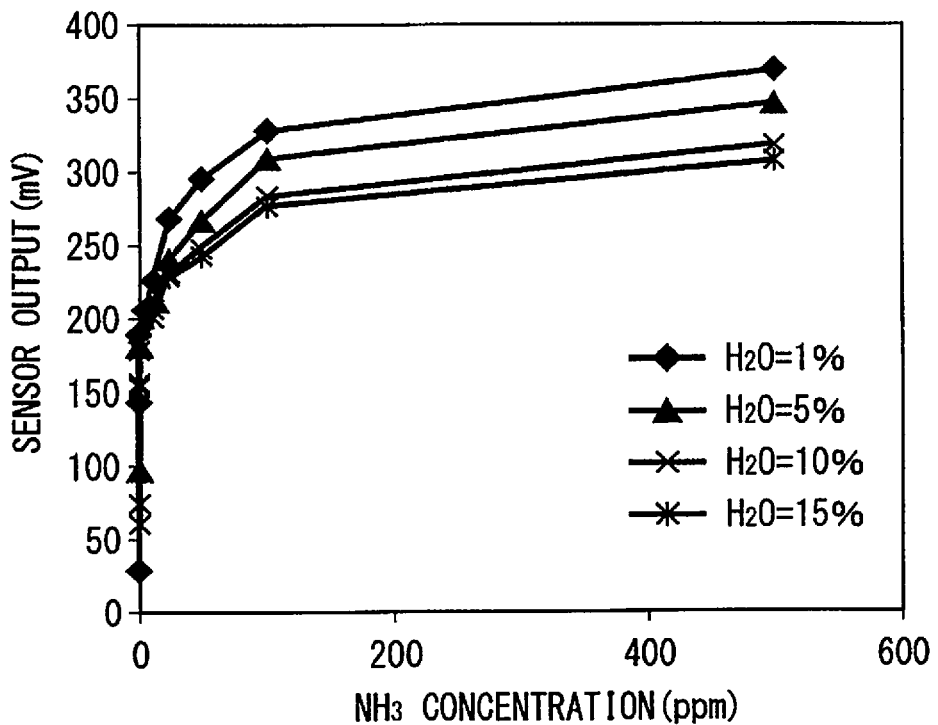
FIGS. 7A and 7B show a change of the sensor output with respect to the concentration of an ammonia gas, which is plotted for each gas atmosphere with the same concentration of water vapor, where the gas sensor 100A is driven at an element control temperature of 380° C.
Figure 7B:
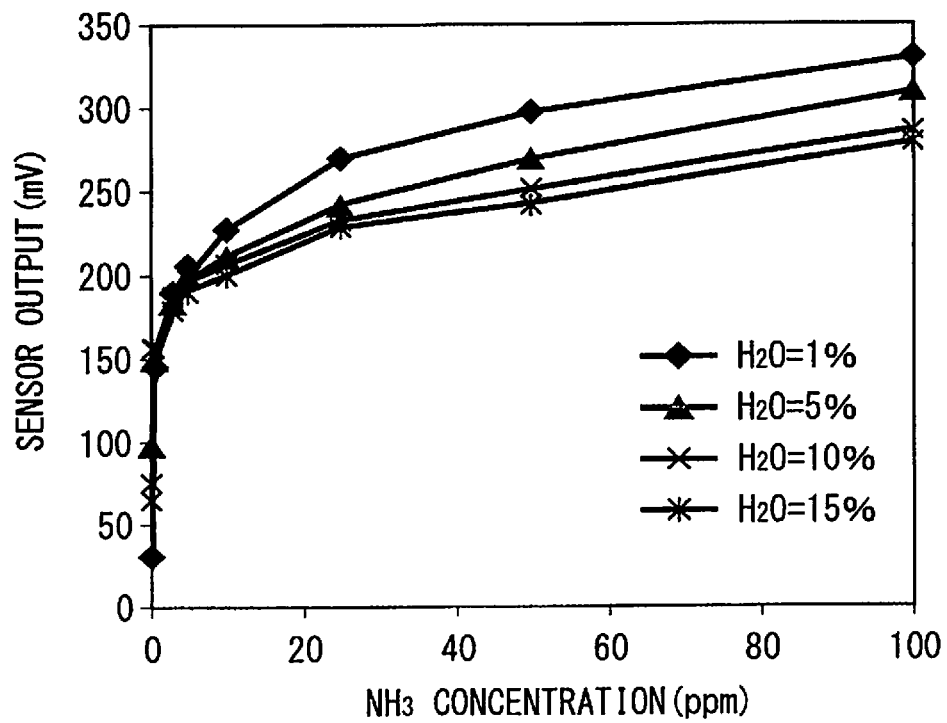
Figure 8A:
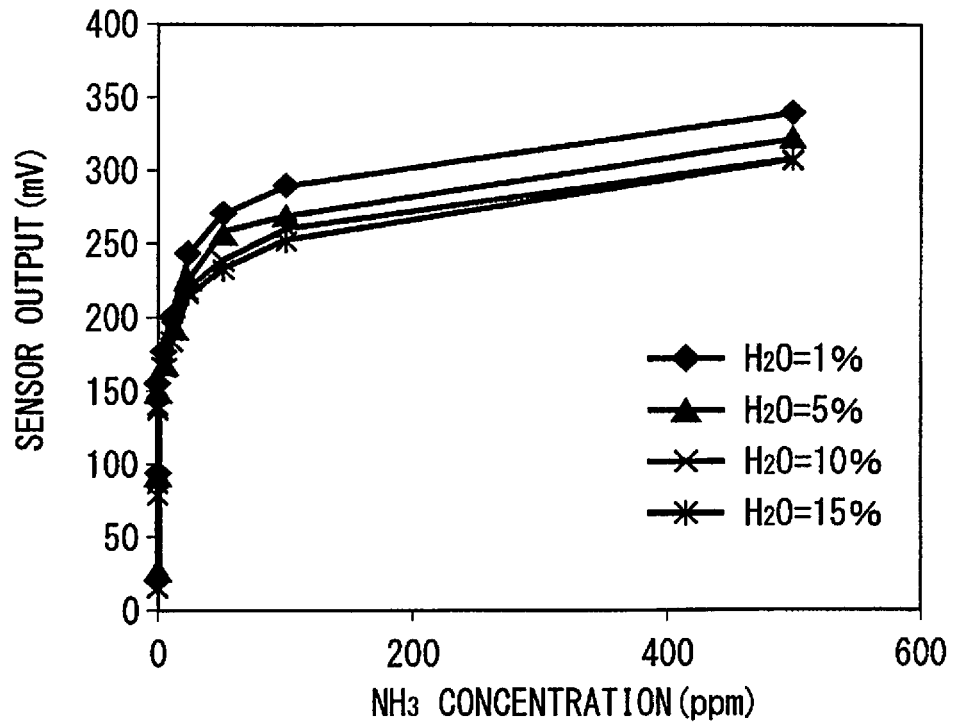
FIGS. 8A and 8B show a change of the sensor output with respect to the concentration of an ammonia gas, which is plotted for each gas atmosphere with the same concentration of water vapor, where the gas sensor 100A is driven at an element control temperature of 420° C.
Figure 8B:
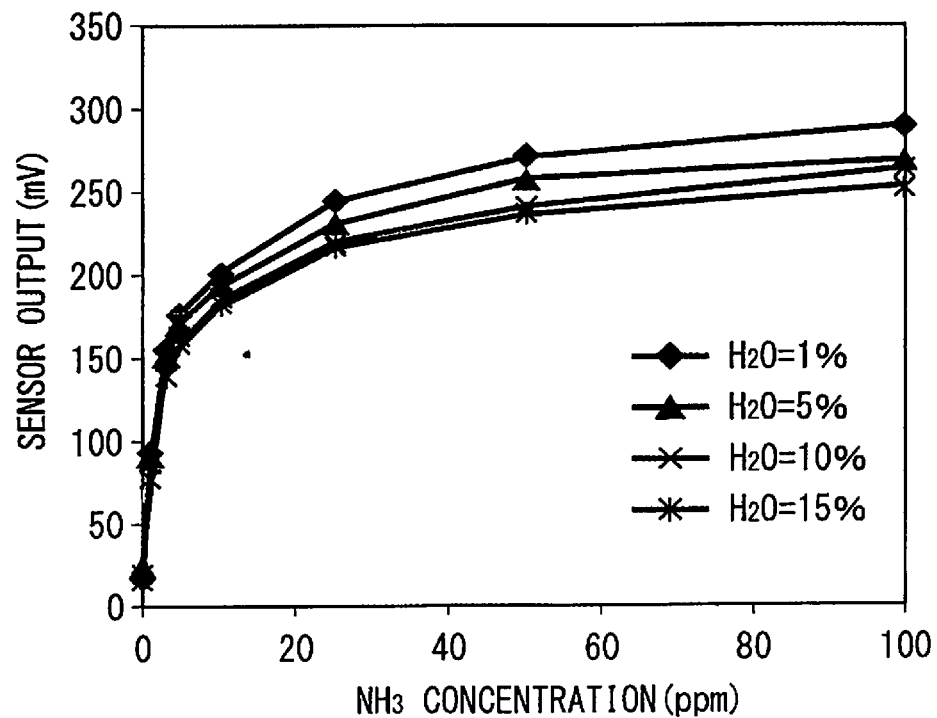
Figure 9A:
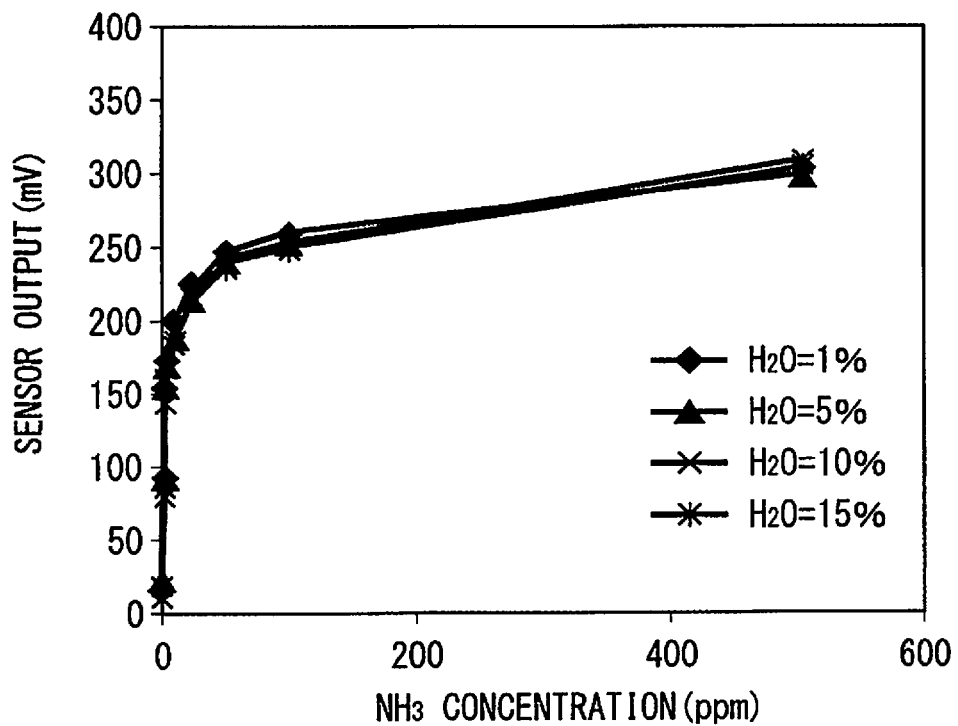
FIGS. 9A and 9B show a change of the sensor output with respect to the concentration of an ammonia gas, which is plotted for each gas atmosphere with the same concentration of water vapor, where the gas sensor 100A is driven at an element control temperature of 450° C.
Figure 9B:
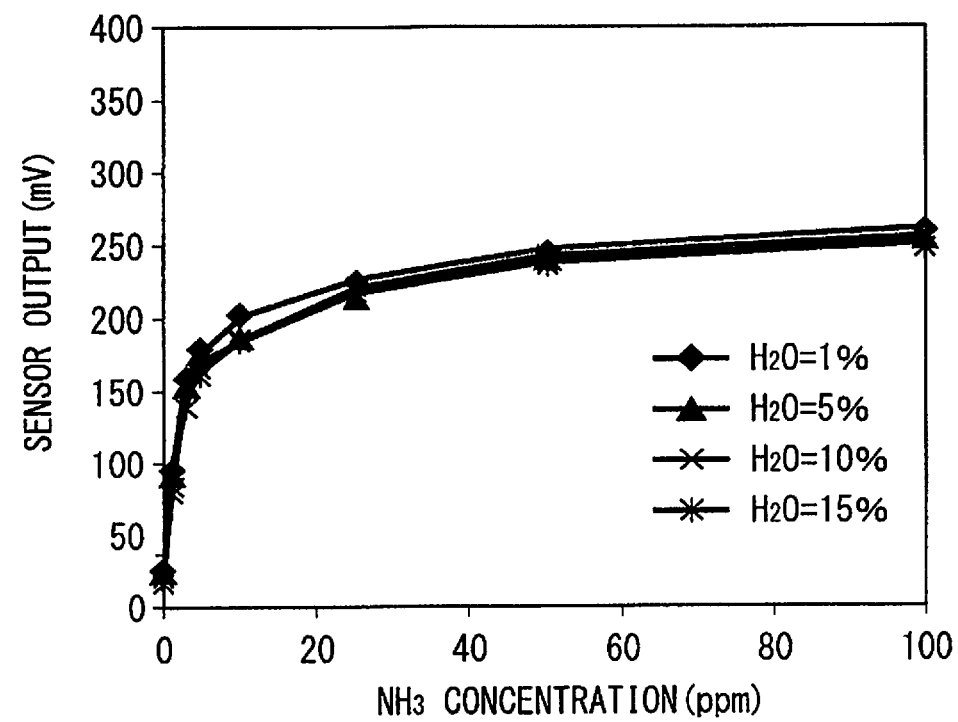
Figure 10A:
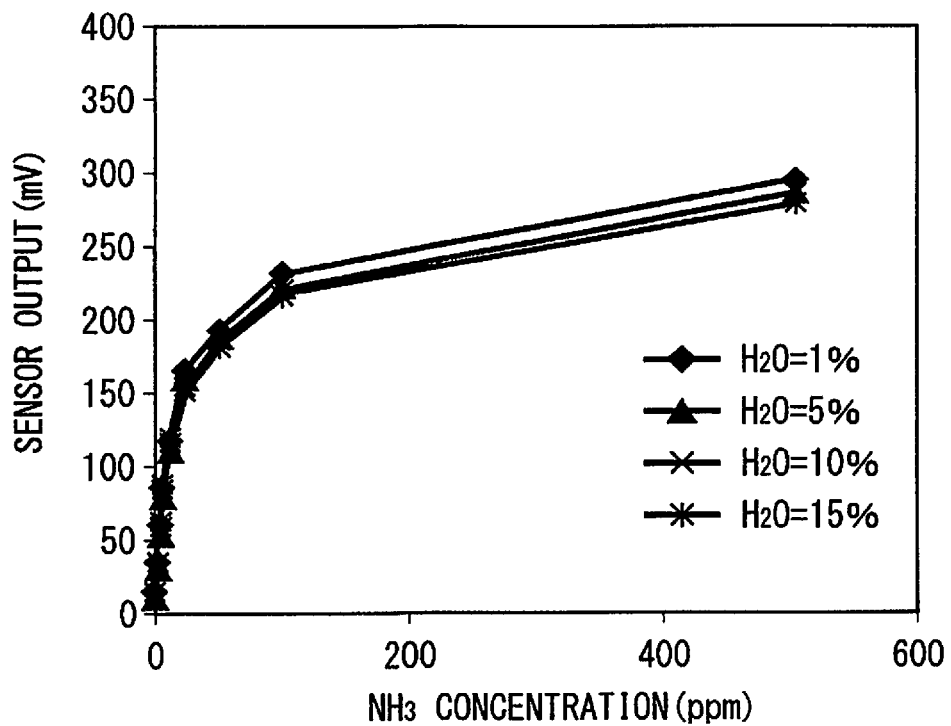
FIGS. 10A and 10B show a change of the sensor output with respect to the concentration of an ammonia gas, which is plotted for each gas atmosphere with the same concentration of water vapor, where the gas sensor 100A is driven at an element control temperature of 5000° C.
Figure 10B:
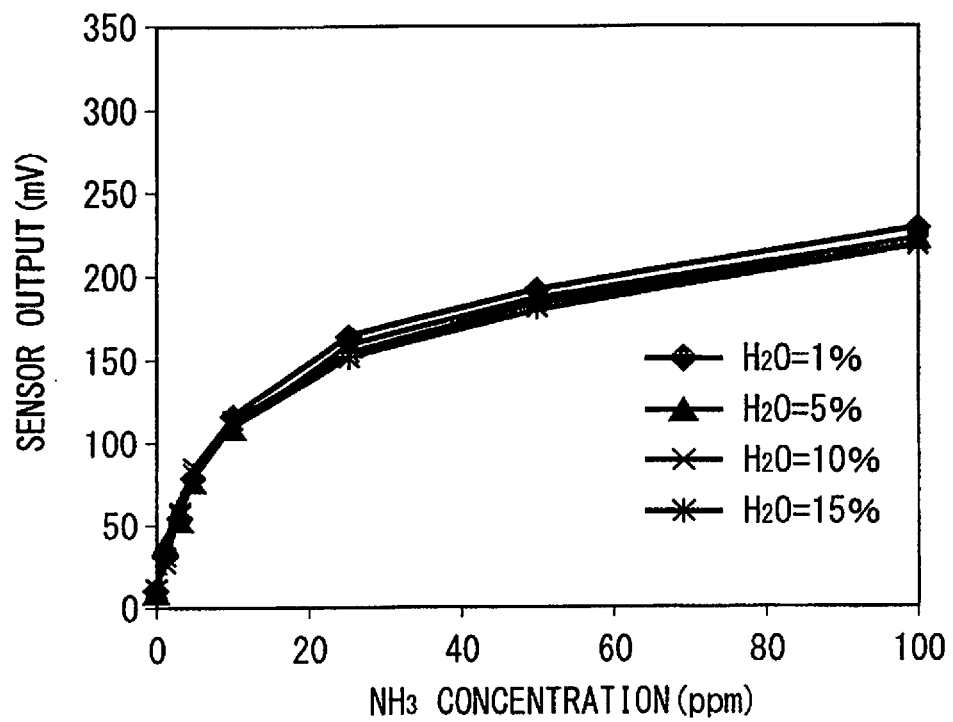
Figure 11A:
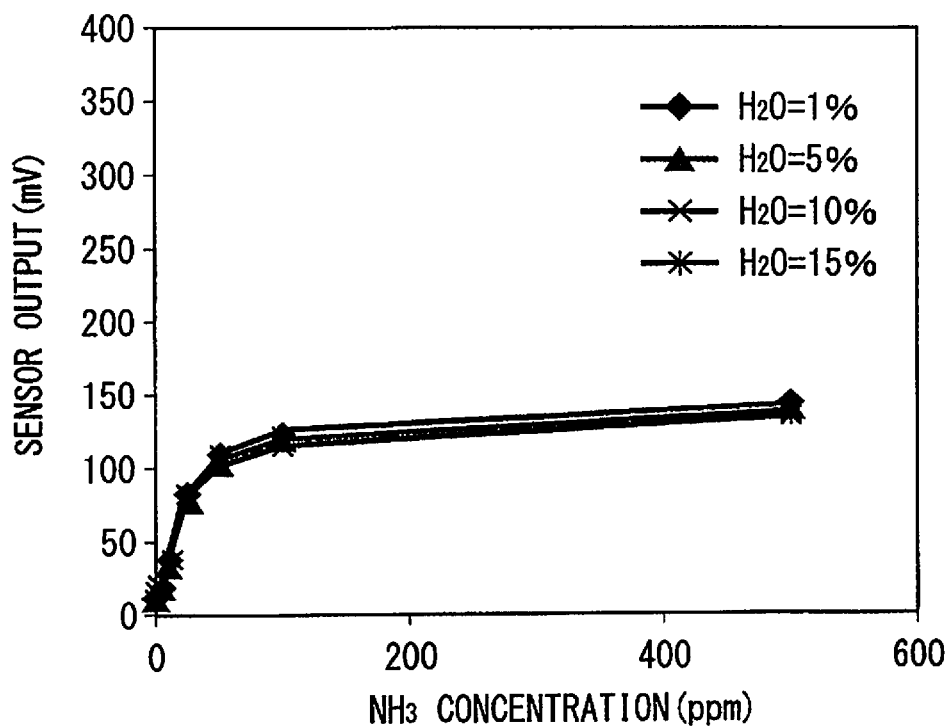
FIGS. 11A and 11B show a change of the sensor output with respect to the concentration of an ammonia gas, which is plotted for each gas atmosphere with the same concentration of water vapor, where the gas sensor 100A is driven at an element control temperature of 650° C.
Figure 11B:
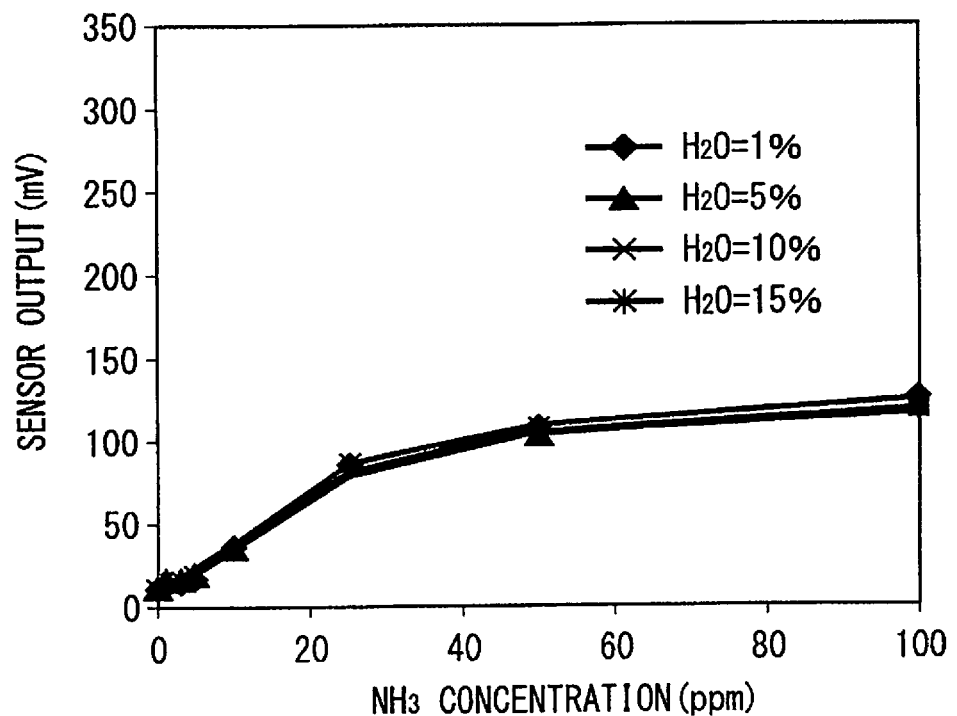

FIGS. 5A, 5B and 5C show sensitivity characteristics to an ammonia gas and sensitivity characteristics to an ethylene ($C_2H_4$) gas being one of hydrocarbon gases for three gas sensors 100A having different porosities of the surface protective layer 50. FIGS. 5A, 5B and 5C show results, respectively, for the gas sensor 100A which is not provided with the surface protective layer 50 (which can be supposed to have a porosity of 100%), the gas sensor 100A in which the porosity of the surface protective layer 50 is 40%, and the gas sensor 100A in which the porosity of the surface protective layer 50 is 12%.

Conditions for measurement of the sensor output in obtaining the respective sensitivity characteristics are as follows. The Au abundance ratio is about 0.5 for all of the above-mentioned gas sensors 100A.

Element control temperature: 500° C.;
Gas atmosphere: $O_2$=10%, $H_2O$=5%, $NH_3$ or $C_2H_4$=0-100 ppm (25 ppm step for $NH_3$; $C_2H_4$ is set at the same concentration as that of $NH_3$ except for 25 ppm), balance: $N_2$;
Gas flow rate: 0.5 L/min;
Pressure: 1 atm;
Surface protective layer: thickness: 10 μm.

The porosity was evaluated through an analysis of a 7500 times-magnified image of A SEM image of a cross-section of the surface protective layer 50 taken under the condition of an accelerating voltage of 5 kV.

In all of FIGS. 5A, 5B and 5C, the sensor output increases as the concentration becomes higher for both the ammonia gas and the ethylene gas, and comparison at the same concentration renders that the output value for the ammonia gas is larger. In the case of the ethylene gas, the rate of change (slope) of the sensor output with respect to the concentration value is almost constant, whereas in the case of the ammonia gas, the change of the sensor output is the largest over a concentration range of 0 ppm to 25 ppm, and the rate of change is smaller over a concentration range above 25 ppm.

For avoiding interference of the ethylene gas to sensing of the ammonia gas, it is desired that the output value in the sensitivity characteristics for the ammonia gas be as large as possible, and the difference between the output value for the ammonia gas and the output value for the ethylene gas be as large as possible.

Comparison of FIGS. 5A, 5B and 5C from this point of view renders that in the case of FIG. 5A showing sensitivity characteristics in the gas sensor 100A which is not provided with the surface protective layer 50, the difference between the sensor output values for the ammonia gas and the ethylene gas is smaller as compared to FIGS. 5B and 5C over the whole range of up to 100 ppm, and worse still, the sensor output value for the ethylene gas at a concentration of 100 ppm is almost comparable to the sensor output value for the ammonia gas at a concentration of 25 ppm.

Such a gas sensor 100A cannot be said to reliably sense the ammonia gas unless it is ensured that the concentration difference between the ammonia gas and the ethylene gas which exist in the measurement gas is sufficiently large.

On the other hand, in the case of FIG. 5B where the surface protective layer 50 having a porosity of 40% is provided and in the case of FIG. 5C where the surface protective layer 50 having a porosity of 12% is provided, the value of the sensor output for the ethylene gas even at a concentration of 100 ppm is smaller than the sensor output value for the ammonia gas at a concentration of 25 ppm.

This means that when the gas sensor 100A includes the surface protective layer 50, and the porosity of the surface protective layer 50 is at least in a range of not more than 40%, an ammonia gas can be reliably sensed when existing at a concentration of at least 25 ppm even if a hydrocarbon gas exists at a maximum concentration of 100 ppm. In such a case, the calculated ammonia gas concentration may include an error, but it can be said from comparison between FIG. 5A and FIGS. 5B and 5C that the maximum error is reduced as compared to the gas sensor 100A which does not include the surface protective layer 50. Thus, it can be said that the gas sensor 100A including the surface protective layer 50 having a porosity of 40% or less for protecting the sensing electrode 10 due to the above-described reason is less likely to be influenced by interference from a hydrocarbon gas contained in a measurement gas, as compared to the gas sensor 100A which does not include the surface protective layer 50.

Of course, it is evident from the sensitivity characteristics shown in FIGS. 5B and 5C that when interference from a hydrocarbon gas and other gases is not a problem, the concentration of a smaller amount of an ammonia gas can be measured.

While FIGS. 5A, 5B and 5C show results in the gas sensor 100A, the arrangement relation between the surface protective layer 50 and the sensing electrode 10 in the gas sensors 100B and 100C is similar to that in the gas sensor 100A, and therefore in the gas sensors 100B and 100C, an effect similar to that of the gas sensor 100A can be obtained in regard to the surface protective layer 50.

In actual situation using the gas sensors 100A to 100C, interference between an ammonia gas and a hydrocarbon gas is thought to occur when an ammonia gas and a hydrocarbon gas that are contained in a measurement gas arrive at the sensing electrode 10 at the same time. But, since the sensor elements 101A to 101C are configured such that the porosity of the surface protective layer 50 is set to 40% or less, an ammonia gas priorly arrives at the sensing electrode 10. From such a point of view, the gas sensors 100A to 100C have reduced influences of interference from a hydrocarbon gas.

Specifically, in the sensor elements 101A to 101C, the porous surface protective layer 50 is provided so as to cover the sensing electrode 10, and therefore an external measurement gas arrives at the sensing electrode 10 by passing pores formed in a network shape inside the surface protective layer 50. The measurement gas contains some gas components, the speeds of individual gas components for arriving at the sensing electrode 10 by passing through the surface protective layer 50 are not the same, and a gas component having a smaller molecular weight has a higher arrival speed because the gas component has a smaller molecular size. For example, the molecular weight of ammonia is 17, whereas in the case of a hydrocarbon gas contained in an exhaust gas from an internal combustion engine, even ethylene having a small molecular size has a molecular weight of 28, and a hydrocarbon gas having a larger molecular weight may be generated. Therefore, an ammonia gas arrives at the sensing electrode 10 prior to a hydrocarbon gas.

Thus, when the concentration is intermittently measured at predetermined intervals, a sensor output that is first generated in each measuring timing is derived from an ammonia gas. When the concentration is calculated on the basis of such a sensor output, influences of a hydrocarbon gas can be eliminated to perform accurate calculation.

(Interference from Water Vapor)

FIG. 6 shows a change of the sensor output with respect to the concentration of water vapor at each element control temperature, which is plotted with the abscissa set to a logarithmic scale, where the gas sensor 100A is driven at different element control temperatures under a plurality of gas atmospheres having the same concentration of an ammonia gas and different concentrations of water vapor (concentration of H₂O).

Conditions for measurement of the sensor output in obtaining the respective sensor outputs are as follows. The Au abundance ratio in the sensing electrode 10 of the gas sensor 101A used is 0.99, and the porosity of the surface protective layer 50 is 12%.

Element control temperature: 380° C., 420° C., 450° C. to 750° C. (50° C. step);
Gas atmosphere: $O_2$=10%, $H_2O$=1%, 5%, 10%, 15%, $NH_3$=100 ppm, balance: $N_2$;
Gas flow rate: 0.5 L/min;
Pressure: 1 atm;
Surface protective layer: thickness: 10 µm.

From FIG. 6, it is apparent that while the sensor output tends to decrease as the element control temperature becomes higher, the sensor output value tends to vary particularly in a range with a low concentration of water vapor as the element control temperature becomes lower, and such a variation is noticeable when the element control temperature is 420° C. or lower. Since the concentration of an ammonia gas is constant at 100 ppm, such a variation is considered to be caused by a difference in concentration of water vapor. The concentration of water vapor in an exhaust gas is normally about 5% to 15%, and therefore in the case of measuring the concentration of an ammonia gas in an exhaust gas, such a variation indicates that the concentration of water vapor may influence accuracy of the concentration of an ammonia gas, that is, interference from a water vapor gas occurs in measurement of an ammonia gas.

In view of the results shown in FIG. 6, it can be said that the element control temperature is preferably 450° C. or higher and lower than 700° C., more preferably 450° C. or higher and 650° C. or lower for eliminating influences of interference from water vapor in measurement of the concentration of an ammonia gas. This is because, when the element control temperature is set within such a range, the sensor output is almost constant independently of the concentration of water vapor as long as the concentration of an ammonia gas is constant.

This is shown by FIGS. 7A, 7B, 8A, 8B, 9A, 9B, 10A, 10B, 11A, 11B, 12A and 12B. FIGS. 7A and 7B, FIGS. 8A and 8B, FIGS. 9A and 9B, FIGS. 10A and 10B, FIGS. 11A and 11B and FIGS. 12A and 12B show a change of the sensor output with respect to the concentration of an ammonia gas, which is plotted for each gas atmosphere with the same concentration of water vapor, where the gas sensor 100A is driven at various element control temperatures in the range of 380° C. to 750° C. under a plurality of gas atmospheres having different concentrations of an ammonia gas and different concentrations of water vapor. Specifically, FIGS. 7A and 7B, FIGS. 8A and 8B, FIGS. 9A and 9B, FIGS. 10A and 10B, FIGS. 11A and 11B and FIGS. 12A and 12B show results at element control temperatures of 380° C., 420° C., 450° C., 500° C., 650° C. and 750° C., respectively. FIGS. 7B, 8B, 9B, 10B, 11B and 12B are graphs obtained by enlarging a part of FIGS. 7A, 8A, 9A, 10A, 11A and 12A, respectively.

Conditions for measurement of the sensor output in obtaining the respective sensor outputs are as follows. The Au abundance ratio in the sensing electrode 10 of the gas sensor 101A used is 0.99, and the porosity of the surface protective layer 50 is 12%.

Gas atmosphere: $O_2$=10%, $H_2O$=1%, 5%, 10%, 15%, $NH_3$=0 ppm, 1 ppm, 3 ppm, 5 ppm, 10 ppm, 25 ppm, 50 ppm, 100 ppm, 500 ppm, balance: $N_2$;
Gas flow rate: 0.5 L/min;
Pressure: 1 atm;
Surface protective layer: thickness: 10 µm.

Comparison of FIGS. 7A and 7B, FIGS. 8A and 8B, FIGS. 9A and 9B, FIGS. 10A and 10B, FIGS. 11A and 11B and FIGS. 12A and 12B renders that first, when the element control temperature is 380° C. or 420° C. as shown in FIGS. 7A and 7B or FIGS. 8A and 8B, the sensor output depends on the concentration of an ammonia gas while also being influenced by the variation in concentration of water vapor.

On the other hand, when the element control temperature is 450° C., 500° C. or 650° C. as shown in FIGS. 9A and 9B, FIGS. 10A and 10B or FIGS. 11A and 11B, the sensor output depends on the concentration of an ammonia gas, and almost the same level of a sensor output is obtained independently of the concentration of water vapor over the whole ammonia concentration range of 0 ppm to 500 ppm. The error is at most about 10 mV, and this level of error is allowable in light of expected measurement accuracy in the gas sensor 100A.

Figure 12A:
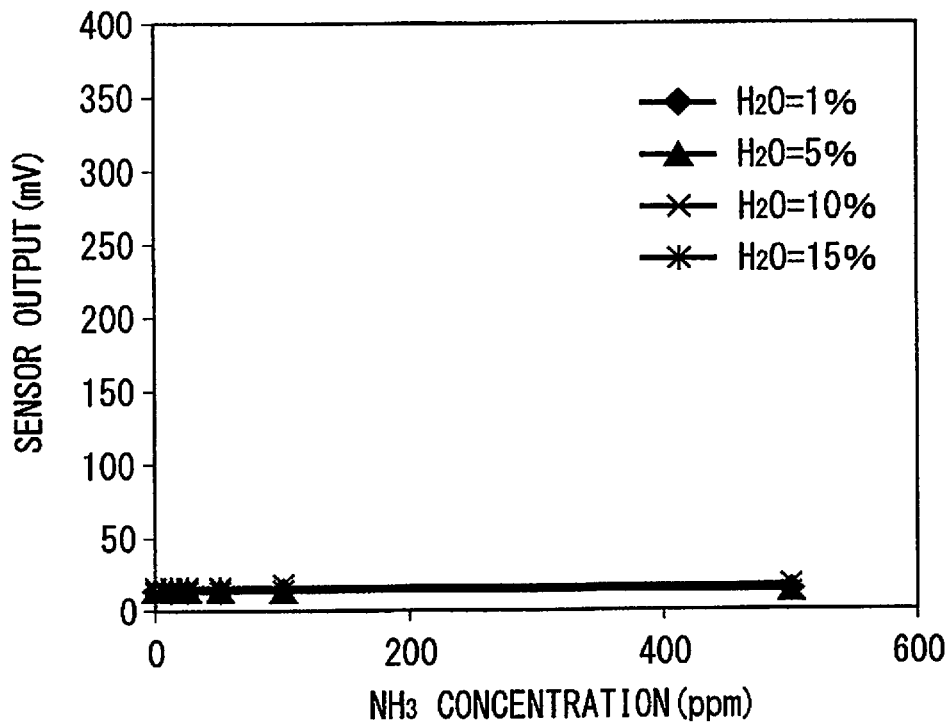
FIGS. 12A and 12B show a change of the sensor output with respect to the concentration of an ammonia gas, which is plotted for each gas atmosphere with the same concentration of water vapor, where the gas sensor 100A is driven at an element control temperature of 750° C.
Figure 12B:
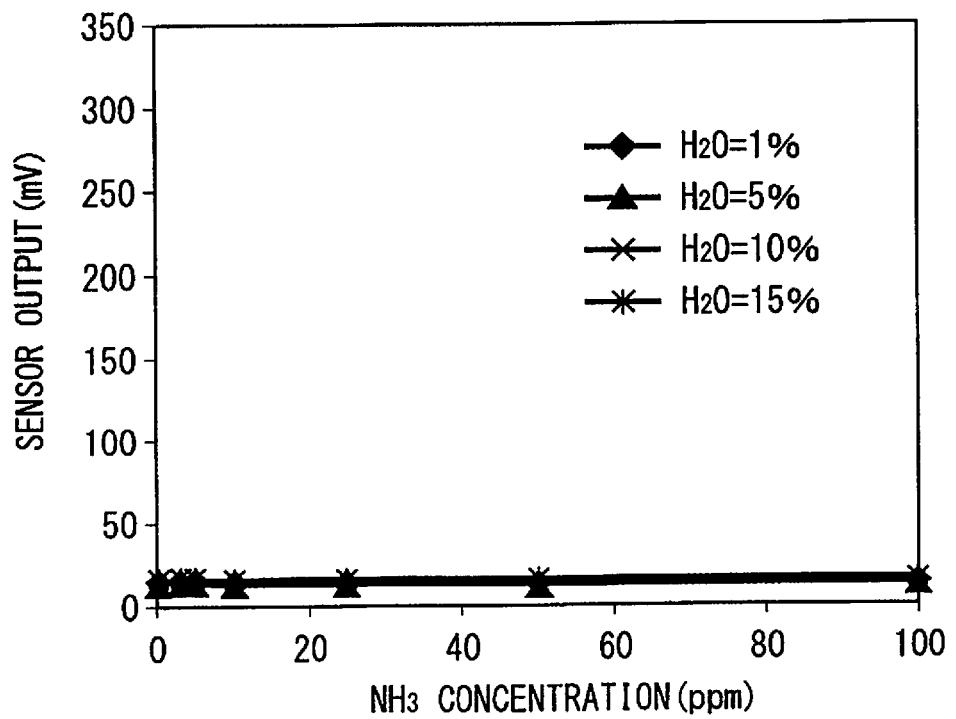

In contrast, when the element control temperature is 750° C. as shown in FIGS. 12A and 12B, the sensor output does not depend on either the concentration of an ammonia gas or the concentration of water vapor, and is substantially constant at a small value of about 15 mV.

That is, the results shown in FIGS. 7A, 7B, 8A, 8B, 9A, 9B, 10A, 10B, 11A, 11B, 12A and 12B show that by appropriately setting the element control temperature within the range of 450° C. or higher and lower than 700° C., preferably within the range of 450° C. or higher and 650° C. or lower, the concentration of an ammonia gas can be measured without considering interference of water vapor.

The element control temperature is considered to be preferably 450° C. or higher and lower than 700° C. for eliminating influences of interference from water vapor in measurement of the concentration of an ammonia gas as described above, but it is not necessarily unable to measure an ammonia gas when the element control temperature is 700° C. or higher. That is, when the element control temperature is 700° C. or higher, the sensor output itself decreases while influences of interference from water vapor decrease, but when the concentration of an ammonia gas is in a range above 100 ppm, the sensor output is larger than the value shown in FIG. 6, it is therefore possible to make a measurement in this concentration range in principle, and thus it is not necessarily unable to measure an ammonia gas.

While FIGS. 6, 7A, 7B, 8A, 8B, 9A, 9B, 10A, 10B, 11A, 11B, 12A and 12B show results in the gas sensor 100A, setting of the element control temperature in the gas sensors 100B and 100C is performed in the same manner as in the gas sensor 100A, and therefore in the gas sensors 100B and 100C, an effect similar to that of the gas sensor 100A can be obtained when the element control temperature is 450° C. or higher and lower than 700° C., preferably 450° C. or higher and 650° C. or lower.

In actual situation using the gas sensors 100A to 100C, interference to an ammonia gas from a water vapor gas does not necessarily occur independently of interference from a hydrocarbon gas described above, and normally both the interferences occur concurrently. However, the sensor output is independent of the concentration of a water vapor gas when the element control temperature is appropriately set as described above, so, in the case that the porosity of the surface protective layer 50 is preferably set within a range of 5% or more and 40% or less, the concentration of an ammonia gas can be measured while interference from a hydrocarbon gas is minimized, even if both a water vapor gas and a hydrocarbon gas exist in addition to an ammonia gas in a measurement gas.

Process of Manufacturing Sensor Element

Next, the process of manufacturing the sensor elements 101A to 101C will be described using an example case where these sensor elements have the layer structures as illustrated in FIGS. 1A, 1B, 2A, 2B, 3A, and 3B. Generally speaking, the sensor elements 101A to 101C as illustrated in FIGS. 1A, 1B, 2A, 2B, 3A, and 3B are each manufactured by forming a laminated body formed of green sheets containing an oxygen-ion conductive solid electrolyte such as zirconia as a ceramic component and by cutting and firing the laminated body. The oxygen-ion conductive solid electrolyte may be, for example, yttrium partially stabilized zirconia (YSZ).

Figure 13:
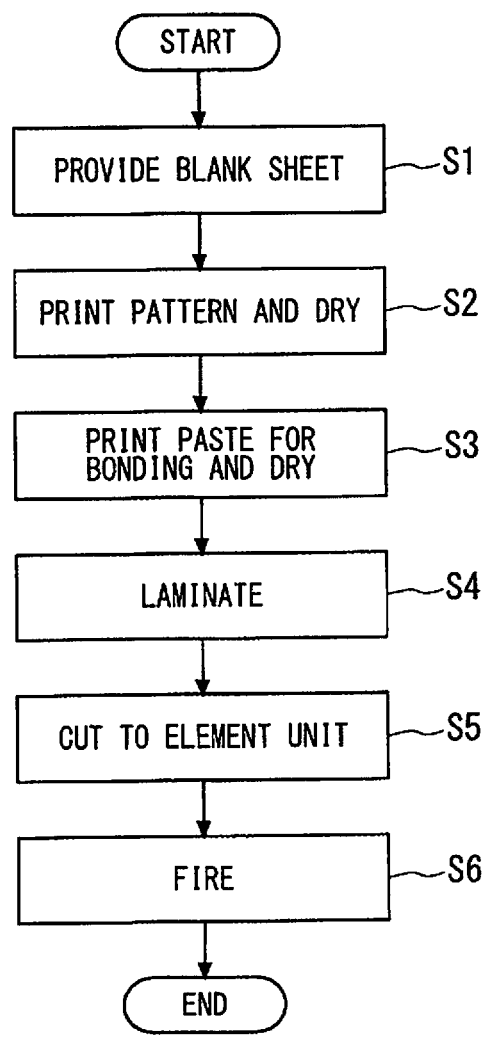
FIG. 13 shows a flow of the process of preparing the sensor elements 101A to 101C.

FIG. 13 is a flowchart illustrating the process of manufacturing the sensor elements 101A to 101C. In the manufacture of the sensor elements 101A to 101C, first, blank sheets (not shown) that are green sheets having no pattern formed thereon are prepared (step S1). Specifically, six blank sheets corresponding to the first to sixth solid electrolyte layers 1 to 6 are prepared. A blank sheet for forming the surface protective layer 50 is prepared as well. A plurality of sheet holes used for positioning in printing and lamination are provided in the blank sheets. Such sheet holes are formed in advance through, for example, punching by a punching machine. For a green sheet whose corresponding layer forms an internal space, a penetration corresponding to the internal space is also provided in advance through, for example, punching as described above. All the blank sheets corresponding to the respective layers of the sensor elements 101A to 101C need not to have the same thickness.

After the preparation of the blank sheets corresponding to the respective layers, pattern printing and drying are performed to form various patterns on the individual blank sheets (step S2). Specifically, electrode patterns of, for example, the sensing electrode 10 and the reference electrode 20, the reference gas introduction layer 30, internal wiring (not shown), and the like are formed. In the first solid electrolyte layer 1, a cut mark is printed that serves as a reference cut position when the laminated body is cut in a subsequent step.

Each pattern is printed by applying a paste for pattern formation, prepared in accordance with the characteristic required for each formation target, to the blank sheet by a known screen printing technique. Any known drying means is available for drying after printing.

The sensor elements 101A to 101C are characterized by the way of preparing a conductive paste used to form the sensing electrode 10. This will be described below in detail.

After the pattern printing, printing and drying of a bonding paste are performed to laminate and bond the green sheets corresponding to the respective layers (step S3). Any known screen printing technique is available for printing of a bonding paste, and any known drying means is available for drying after printing.

Subsequently, crimping is performed in which the adhesive-applied green sheets are laminated in a predetermined order, and the laminated green sheets are crimped on the predetermined temperature and pressure conditions, to thereby form a laminated body (step S4). Specifically, green sheets that are lamination targets are laminated while being positioned at the sheet holes to be held in a predetermined lamination jig (not shown), and the green sheets together with the lamination jig are heated and pressurized by a lamination machine such as a known hydraulic pressing machine. The pressure, temperature, and time for heating and pressurizing depend on a lamination machine to be used, whose conditions may be set appropriately for good lamination.

After the laminated body has been obtained as described above, subsequently, a plurality of parts of the laminated body are cut out as individual units (referred to as element bodies) of the sensor elements 101A to 101C (step S5). The cut out element bodies are fired under predetermined conditions, thereby producing the sensor elements 101A to 101C as described above (step S6). In other words, the sensor elements 101A to 101C are produced by co-firing the solid electrolyte layers and the electrodes. The firing temperature is preferably 1200° C. or higher and 1500° C. or lower (for example, 1400° C.). The integral firing performed in such a manner provides satisfactory adhesion strength to the respective electrodes of the sensor elements 101A to 101C. This contributes to improvement of durability of the sensor elements 101A to 101C.

The resultant sensor elements 101A to 101C are housed in a predetermined housing and incorporated into main bodies (not shown) of the gas sensors 100A to 100C.

Conductive Paste for Forming Sensing Electrode

Next, a conductive paste used to form the sensing electrode 10 will be described. The conductive paste for forming a sensing electrode is produced by using a Au ion-containing liquid as a Au starting material and mixing the Au ion-containing liquid with powdered Pt, powdered zirconia, and a binder. Any binder, which can disperse any other row material to the printable extent and vanishes through firing, may be appropriately selected. The production of a conductive paste in such a manner is referred to as liquid-state Au mixing.

Here, the Au ion-containing liquid is obtained by dissolving a salt containing a Au ion or an organometallic complex containing a Au ion in a solvent. The Au ion-containing salt may be, for example, tetrachloroauric(III) acid ($HAuCl_4$), sodium chloroaurate(III) ($NaAuCl_4$), or potassium dicyanoaurate(I) ($KAu(CN)_2$). The Au ion-containing organometallic complex may be, for example, gold(III) diethylenediamine trichloride ($[Au(en)_2]Cl_3$), gold(III) dichloro(1,10-phenanthroline)chloride ($[Au(phen)Cl_2]Cl$), dimethyl (trifluoroacetylacetonate)gold, or dimethyl (hexafluoroacetylacetonate)gold. Tetrachloroauric(III) acid or gold(III) diethylenediamine chloride ($[Au(en)_2]Cl_3$) is preferably used from the viewpoint of no impurity such as Na or K remaining in the electrode, easy handling, or dissolvability in the solvent. The solvent may be acetone, acetonitrile, or formamide as well as alcohols such as methanol, ethanol, and propanol.

Mixing can be performed by well-known means such as instillation. Although the obtained conductive paste contains Au present in ionic (complex ionic) state, the sensing electrodes 10 formed in the sensor elements 101A to 101C obtained through the above-mentioned manufacturing process contain Au mainly as an elemental substrate or an alloy with Pt.

Figure 14:
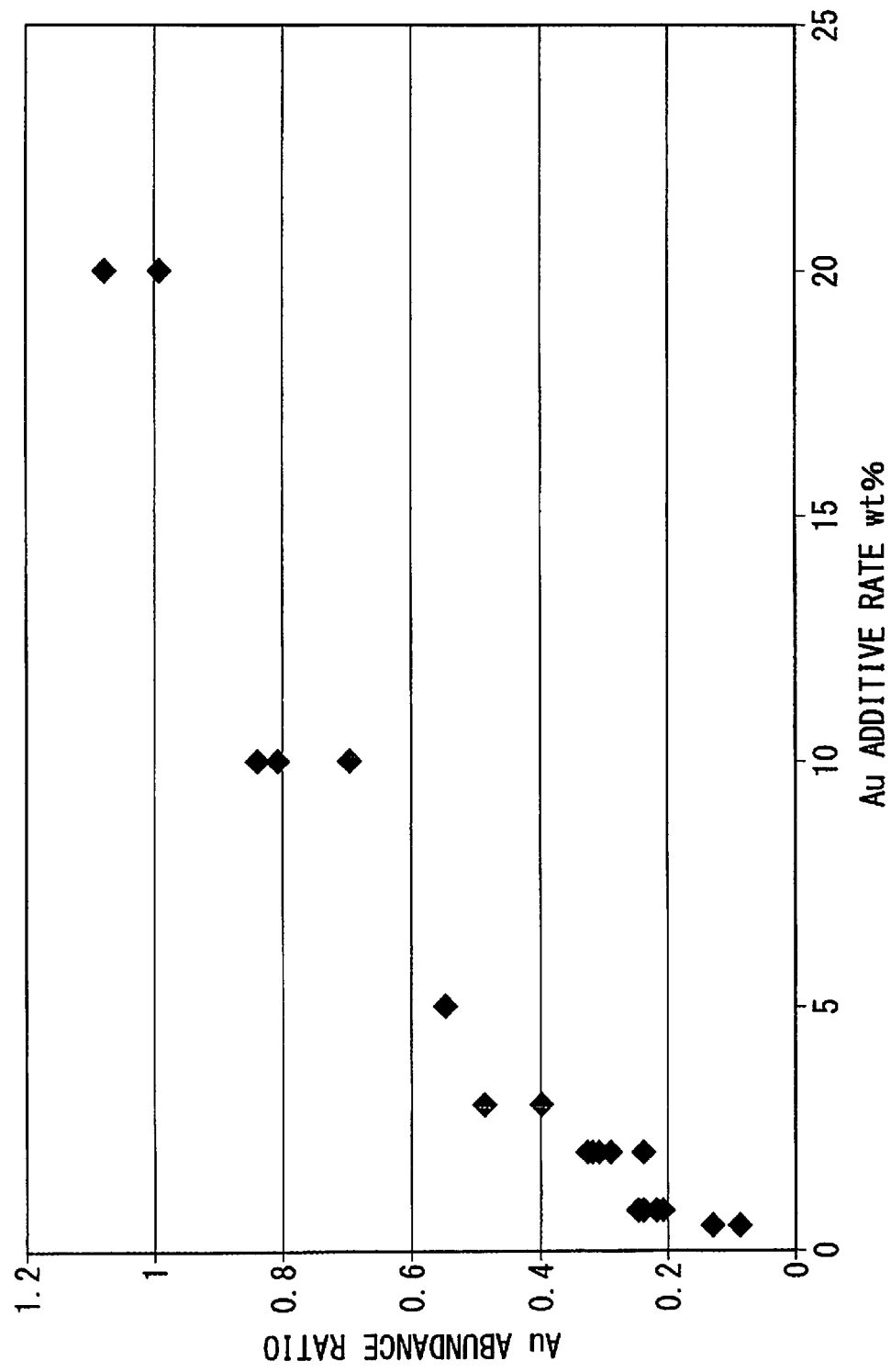
FIG. 14 shows an Au abundance ratio in a sensing electrode 10 formed of a conductive paste for forming a sensing electrode, which is plotted against an Au additive rate, where the conductive paste is prepared through liquid-state Au mixing.

FIG. 14 shows an Au abundance ratio in the sensing electrode 10 formed of a conductive paste for forming a sensing electrode, which is plotted against an Au weight ratio (hereinafter, referred to as an Au additive rate) to the weight of all the noble metal elements (a total weight of Pt and Au) of starting raw materials, where the conductive paste is prepared through liquid-state Au mixing. The Au abundance ratio shown in FIG. 14 is calculated on the basis of XPS analysis.

From FIG. 14, it is apparent that the Au abundance ratio tends to monotonously increase with the Au additive rate and that when the Au additive rate is 3 wt % or more, the sensing electrode 10 having an Au abundance ratio of 0.4 or more can be prepared. A similar result is obtained when the Au abundance ratio is calculated on the basis of AES analysis, although illustration is omitted. In other words, with the use of a conductive paste having an Au additive rate of 3 wt % or more, the sensing electrode 10 having an Au abundance ratio of 0.4 or more can be preferably formed. For example, with the use of a conductive paste having an Au additive rate of 20 wt %, the sensing electrode 10 having an Au abundance ratio of 0.99 or more can be preferably formed.

The value of the Au abundance ratio may be at most 2.4 as described above, and such an upper limit value can be achieved by setting the Au additive rate to 50 wt %.

<Another Way of Preparing Conductive Paste>

In the preparation of a conductive paste for forming a sensing electrode, the paste may be prepared by using coated powder, which is obtained by coating powered Pt with Au, as a starting raw material, instead of preparing the paste through liquid-state Au mixing as described above. In such a case, a conductive paste for a sensing electrode in an inner space is prepared by mixing the coated powder, powdered zirconia, and a binder. Here, the coated powder used in the above preparation may be obtained by covering the particle surface of powered Pt with an Au film or applying Au particles to Pt powder particles.

Also in this case, the sensing electrode 10 having an Au abundance ratio of 0.4 or more and 2.4 or less can be preferably formed.

While the invention has been shown and described in detail, the foregoing description is in all aspects illustrative and not restrictive. It is therefore understood that numerous modifications and variations can be devised without departing from the scope of the invention.

What is claimed is:

1. A mixed-potential gas sensor for sensing an ammonia gas in a measurement gas, said sensor comprising:
    a sensor element composed of an oxygen-ion conductive solid electrolyte, said sensor element comprising:
    a sensing electrode formed of a cermet of a noble metal and an oxygen-ion conductive solid electrolyte, said sensing electrode being provided on a surface of said sensor element;
    a reference electrode formed of a cermet of Pt and an oxygen-ion conductive solid electrolyte; and
    an electrode protective layer being a porous layer that covers at least said sensing electrode, wherein:
    said noble metal consists of noble metal particles,
    an Au abundance ratio in a surface of noble metal particles forming said sensing electrode is 0.4 or more, said Au abundance ratio being an area ratio of a portion of the surface of the noble metal particles covered with said Au to a portion of the surface of the noble metal particles at which said Pt is exposed,
    said noble metal particles consist of Pt and Au,
    a porosity of said electrode protective layer is 5% or more and 40% or less,
    said gas sensor determines a concentration of said ammonia gas on the basis of a potential difference between said sensing electrode and said reference electrode, and
    said sensing electrode has a porosity of 10% to 30%.

2. The mixed-potential gas sensor according to claim 1, further comprising:
    a heater which is provided inside said sensor element, and heats said sensor element, wherein
    said sensor element is disposed in said measurement gas and heated to an element control temperature of 400° C. or higher and 800° C. or lower by said heater, and
    said ammonia gas sensor determines the concentration of said ammonia gas on the basis of a potential difference occurring between said sensing electrode and said reference electrode.

3. The mixed-potential gas sensor according to claim 2, wherein
    said element control temperature is 450° C. or higher and lower than 700° C.

4. The mixed-potential gas sensor according to claim 3, wherein
    said element control temperature is 450° C. or higher and 650° C. or lower.

5. The mixed-potential gas sensor according to claim 1, said sensor element further comprising:
    a reference gas introduction space separated from a space in which said measurement gas is present, into which a reference gas is introduced, wherein
    said reference electrode is disposed under an atmosphere of said reference gas.

6. The mixed-potential gas sensor according to claim 5, said sensor element further comprising:
    a reference gas introduction layer being a porous layer that is in communication with said reference gas introduction space, wherein
    said reference electrode is covered with said reference gas introduction layer.

7. The mixed-potential gas sensor according to claim 5, wherein
    said reference electrode is disposed so as to be exposed to said reference gas introduction space.

8. The mixed-potential gas sensor according to claim 1, wherein
    said sensing electrode and said reference electrode are disposed on the surface of said sensor element.

9. The mixed-potential gas sensor according to claim 8, wherein
    said sensing electrode and said reference electrode are covered with the electrode protective layer.

10. A mixed-potential gas sensor for sensing an ammonia gas in a measurement gas, said sensor comprising:
    a sensor element composed of an oxygen-ion conductive solid electrolyte; and
    a heater which is provided inside said sensor element, and heats said sensor element, wherein
    said sensor element comprises:
    a sensing electrode formed of a cermet of a noble metal and an oxygen-ion conductive solid electrolyte, said sensing electrode being provided on a surface of said sensor element; and
    a reference electrode formed of a cermet of Pt and an oxygen-ion conductive solid electrolyte,
    said noble metal consists of noble metal particles,
    an Au abundance ratio in a surface of noble metal particles forming said sensing electrode is 0.4 or more, said Au abundance ratio being an area ratio of a portion of the surface of the noble metal particles covered with said Au to a portion of the surface of the noble metal particles at which said Pt is exposed,
    said noble metal particles consist of Pt and Au,
    said sensor element is disposed in said measurement gas and heated to an element control temperature of 450° C. or higher and lower than 700° C. by said heater, said ammonia gas sensor determines a concentration of said ammonia gas on the basis of a potential difference occurring between said sensing electrode and said reference electrode, and
said sensing electrode has a porosity of 10% to 30%.

11. The mixed-potential gas sensor according to claim 10, wherein
said element control temperature is 450° C. or higher and 650° C. or lower.

12. The mixed-potential gas sensor according to claim 10, said sensor element further comprising:
a reference gas introduction space separated from a space in which said measurement gas is present, into which a reference gas is introduced, wherein
said reference electrode is disposed under an atmosphere of said reference gas.

13. The mixed-potential gas sensor according to claim 12, said sensor element further comprising:
a reference gas introduction layer being a porous layer that is in communication with said reference gas introduction space, wherein
said reference electrode is covered with said reference gas introduction layer.

14. The mixed-potential gas sensor according to claim 12, wherein
said reference electrode is disposed so as to be exposed to said reference gas introduction space.

15. The mixed-potential gas sensor according to claim 10, wherein
said sensing electrode and said reference electrode are disposed on the surface of said sensor element.

16. The mixed-potential gas sensor according to claim 15, wherein
said sensing electrode and said reference electrode are covered with an electrode protective layer.

17. A method for measuring a concentration of an ammonia gas in a measurement gas using a mixed-potential gas sensor, said gas sensor comprising:
a sensor element composed of an oxygen-ion conductive solid electrolyte; and
a heater which is provided inside said sensor element, and heats said sensor element, wherein
said sensor element comprises:
a sensing electrode formed of a cermet of a noble metal and an oxygen-ion conductive solid electrolyte, said sensing electrode being provided on a surface of said sensor element;
a reference electrode formed of a cermet of Pt and an oxygen-ion conductive solid electrolyte; and
an electrode protective layer being a porous layer that covers at least said sensing electrode, wherein:
said noble metal consists of noble metal particles,
an Au abundance ratio in a surface of noble metal particles forming said sensing electrode is 0.4 or more, said Au abundance ratio being an area ratio of a portion of the surface of the noble metal particles covered with said Au to a portion of the surface of the noble metal particles at which said Pt is exposed,
said noble metal particles consist of Pt and Au,
a porosity of said electrode protective layer is 5% or more and 40% or less, and
said sensing electrode has a porosity of 10% to 30%,
said method comprising the steps of:
a) disposing said sensor element in said measurement gas;
b) heating said sensor element disposed in said measurement gas to an element control temperature of 400° C. or higher and 800° C. or lower by said heater; and
c) determining the concentration of said ammonia gas on the basis of a potential difference occurring between said sensing electrode and said reference electrode with said sensor element held at said element control temperature.

18. The method for measuring the concentration of an ammonia gas according to claim 17, wherein
said element control temperature is 450° C. or higher and lower than 700° C.

19. The method for measuring the concentration of an ammonia gas according to claim 18, wherein
said element control temperature is 450° C. or higher and 650° C. or lower.

20. A method for measuring a concentration of an ammonia gas in a measurement gas using a mixed-potential gas sensor, said gas sensor comprising:
a sensor element composed of an oxygen-ion conductive solid electrolyte; and
a heater which is provided inside said sensor element, and heats said sensor element, wherein
said sensor element comprises:
a sensing electrode formed of a cermet of a noble metal and an oxygen-ion conductive solid electrolyte, said sensing electrode being provided on a surface of said sensor element; and
a reference electrode formed of a cermet of Pt and an oxygen-ion conductive solid electrolyte, wherein:
said noble metal consists of noble metal particles,
an Au abundance ratio in a surface of the noble metal particles forming said sensing electrode is 0.4 or more, said Au abundance ratio being an area ratio of a portion of the surface of the noble metal particles covered with said Au to a portion of the surface of the noble metal particles at which said Pt is exposed,
said noble metal particles consist of Pt and Au, and
said sensing electrode has a porosity of 10% to 30%,
said method comprising the steps of:
a) disposing said sensor element in said measurement gas;
b) heating said sensor element disposed in said measurement gas to an element control temperature of 400° C. or higher and 800° C. or lower by said heater; and
c) determining the concentration of said ammonia gas on the basis of a potential difference occurring between said sensing electrode and said reference electrode with said sensor element held at said element control temperature.

21. The method for measuring the concentration of an ammonia gas according to claim 20, wherein
said element control temperature is 450° C. or higher and 650° C. or lower.

22. The mixed-potential gas sensor according to claim 1, wherein
said sensing electrode comprises 20% by volume to 60% by volume of the oxygen-ion conductive solid electrolyte in the cermet.

23. The mixed-potential gas sensor according to claim 1, wherein
said sensing electrode has a substantially rectangular shape.

24. The mixed-potential gas sensor according to claim 10, wherein
said sensing electrode comprises 20% by volume to 60% by volume of the oxygen-ion conductive solid electrolyte in the cermet.

25. The mixed-potential gas sensor according to claim 10, wherein
said sensing electrode has a substantially rectangular shape.

26. The mixed-potential gas sensor according to claim 1, wherein
a thickness of the electrode protective layer is 1 μm to 50 μm, and a pore diameter of the electrode protective layer is 1 μm or less.

27. The method for measuring the concentration of an ammonia gas according to claim 17, wherein
a thickness of the electrode protective layer is 1 μm to 50 μm, and a pore diameter of the electrode protective layer is 1 μm or less.

* * * * *